(12) United States Patent
Akasaka

(10) Patent No.: US 10,620,153 B2
(45) Date of Patent: Apr. 14, 2020

(54) NITROGEN OXIDE BASED GAS SENSOR, OXYGEN PUMP, GAS SENSOR APPARATUS, MANUFACTURING METHOD OF GAS SENSOR APPARATUS, AND SENSOR NETWORK SYSTEM

(71) Applicant: ROHM CO., LTD., Kyoto (JP)

(72) Inventor: Shunsuke Akasaka, Kyoto (JP)

(73) Assignee: ROHM CO., LTD., Kyoto (JP)

( * ) Notice: Subject to any disclaimer, the term of this patent is extended or adjusted under 35 U.S.C. 154(b) by 357 days.

(21) Appl. No.: 15/485,621

(22) Filed: Apr. 12, 2017

(65) Prior Publication Data
US 2017/0299543 A1    Oct. 19, 2017

(30) Foreign Application Priority Data

Apr. 14, 2016 (JP) .................. 2016-080807

(51) Int. Cl.
*G01N 27/407* (2006.01)
*G01N 27/419* (2006.01)
*G01N 33/00* (2006.01)

(52) U.S. Cl.
CPC ....... *G01N 27/4074* (2013.01); *G01N 27/407* (2013.01); *G01N 27/419* (2013.01); *G01N 33/0006* (2013.01); *G01N 33/0037* (2013.01); *G01N 27/4071* (2013.01); *Y02A 50/245* (2018.01)

(58) Field of Classification Search
CPC ......... G01N 27/406–41; G01N 27/419; G01N 33/0037; G01N 33/0006; Y02A 50/245
See application file for complete search history.

(56) References Cited

U.S. PATENT DOCUMENTS

| | | | | |
|---|---|---|---|---|
| 4,770,760 A | * | 9/1988 | Noda | ................. G01N 27/4072 204/425 |
| 5,540,047 A | * | 7/1996 | Dahlheim | .............. B01D 53/30 60/274 |

(Continued)

FOREIGN PATENT DOCUMENTS

| JP | 2001281192 A | 10/2001 |
|---|---|---|
| JP | 2013156259 A | 8/2013 |

(Continued)

OTHER PUBLICATIONS

Takahashi et al., "Thin-film Limiting-current Type Oxygen Sensor", R&D, vol. 27 No. 2, Jun. 1996, pp. 47-57.

(Continued)

*Primary Examiner* — J. Christopher Ball
(74) *Attorney, Agent, or Firm* — Hamre, Schumann, Mueller & Larson, P.C.

(57) ABSTRACT

A nitrogen oxide based gas sensor includes: a substrate provided with a beam structure having a MEMS structure; a heater disposed on the substrate; a lower electrode disposed on the heater, a solid electrolyte layer disposed on the lower electrode; an upper electrode disposed on a surface of the solid electrolyte layer facing the lower electrode and configured to introduce a measurement target gas; a cavity portion formed in the substrate; and a gas flow path disposed so as to connect the cavity portion and the lower electrode, wherein the gas sensor is configured to detect a concentration of nitrogen oxide in the measurement target gas.

17 Claims, 24 Drawing Sheets

(56) References Cited

U.S. PATENT DOCUMENTS

2014/0262827 A1    9/2014  Fix et al.
2015/0377823 A1*  12/2015  Akasaka ............ G01N 27/4065
                                                                    204/406

FOREIGN PATENT DOCUMENTS

| JP | 2014-190939 | 10/2014 | | |
|---|---|---|---|---|
| JP | 2014-190940 | 10/2014 | | |
| JP | 2014196995 A | 10/2014 | | |
| JP | 2015-155887 | 8/2015 | | |
| JP | 2015-215334 | 12/2015 | | |
| WO | WO-2014136329 A1 * | 9/2014 | ......... | G01N 27/4065 |
| WO | 2015158599 A1 | 10/2015 | | |

OTHER PUBLICATIONS

Saji et al., "Thin-film Limiting-current Type NOx Sensor", Chemical Sensors, vol. 20, Supplement B, 2004, pp. 650-651.
Office Action issued in corresponding Japanese Application No. 2016-080807, dated Dec. 10, 2019, with English translation, total 5 pages provided.

* cited by examiner

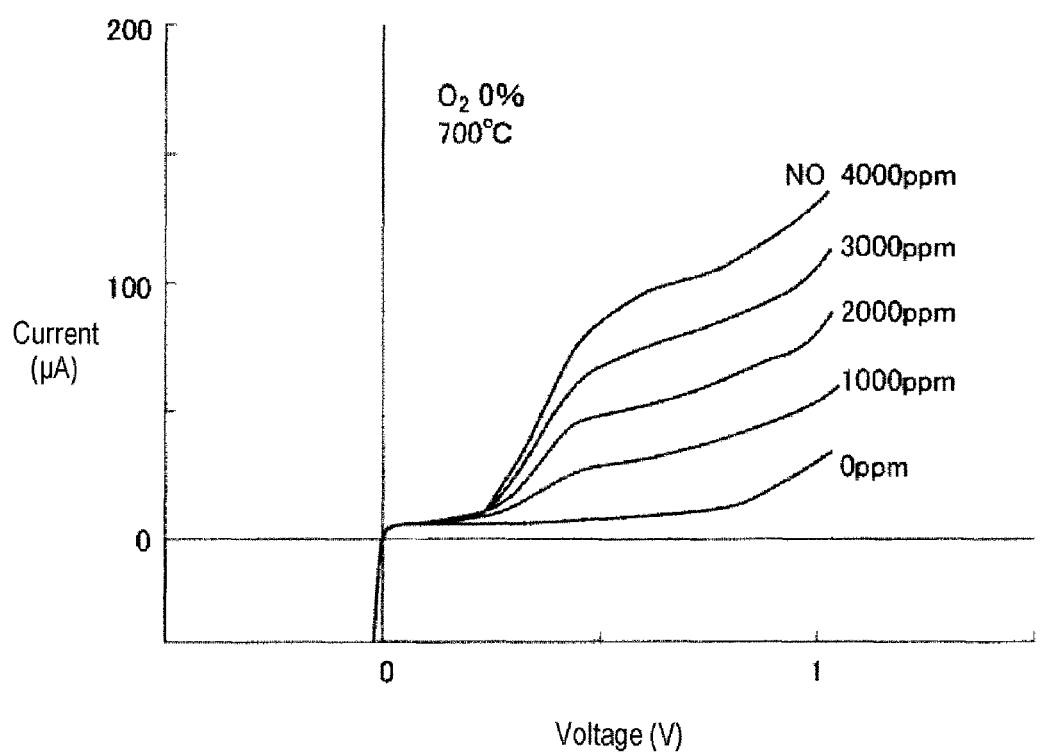

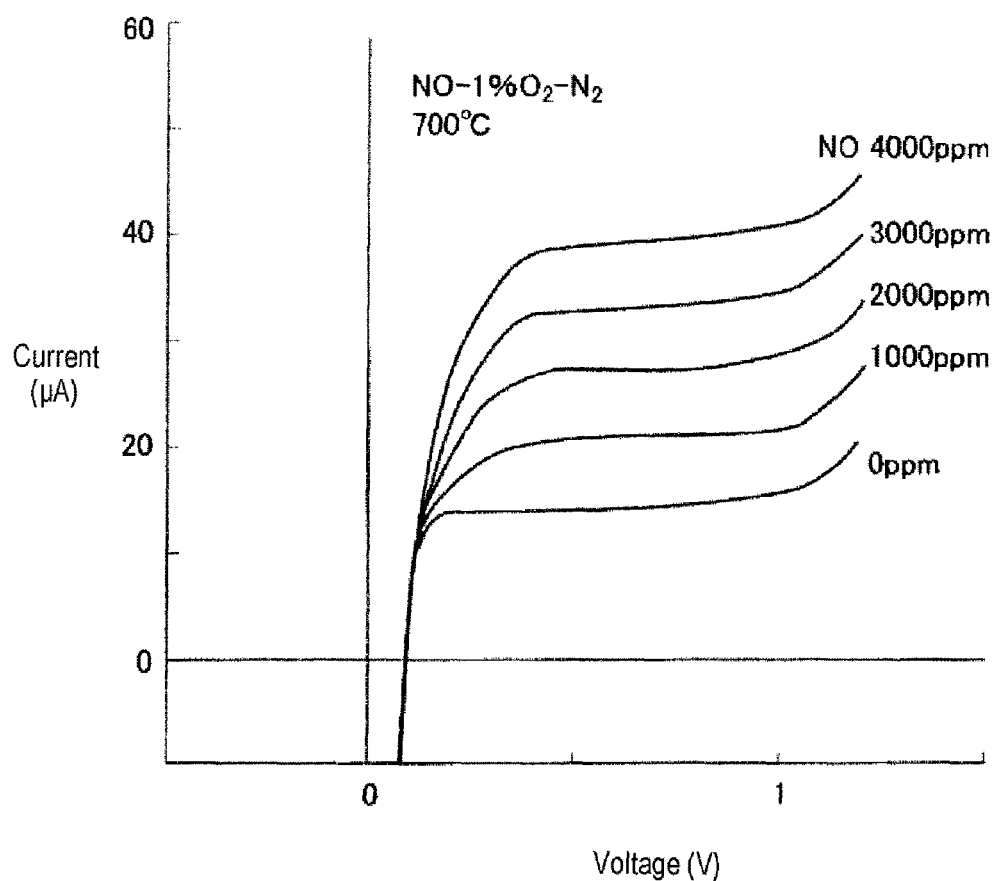

NITROGEN OXIDE BASED GAS SENSOR, OXYGEN PUMP, GAS SENSOR APPARATUS, MANUFACTURING METHOD OF GAS SENSOR APPARATUS, AND SENSOR NETWORK SYSTEM

CROSS-REFERENCE TO RELATED APPLICATION

This application is based upon and claims the benefit of priority from Japanese Patent Application No. 2016-080807, filed on Apr. 14, 2016, the entire contents of which are incorporated herein by reference.

TECHNICAL FIELD

The present disclosure relates to a nitrogen oxide based gas sensor, an oxygen pump, a gas sensor apparatus, a manufacturing method of a gas sensor apparatus, and a sensor network system.

BACKGROUND

There are different types of humidity sensors that detect the concentration of water vapor in a measurement target gas such as a resistance change type, a capacitance change type, a zirconia ($ZrO_2$) solid electrolyte type, or the like. Particularly, in recent years, a zirconia thin film limit current type has attracted attention. This limit current type oxygen sensor has an advantage of high reliability and good linearity.

Furthermore, attempts have been made to apply the zirconia solid electrolyte type to, for example, an in-vehicle $NO_x$ sensor that measures the concentration of nitrogen oxide ($NO_x$ gas) in exhaust gas.

However, in the limit current type gas sensor of the zirconia thin film limit current type, the sensor characteristics need to be further improved and stabilized.

SUMMARY

Some embodiments of the present disclosure provide a nitrogen oxide based gas sensor which is easy to assemble, capable of improving the accuracy of sensing a $NO_x$ gas and capable of increasing the sensitivity of detecting a $NO_x$ gas, an oxygen pump, a gas sensor apparatus, a manufacturing method of a gas sensor apparatus, and a sensor network system to which a gas sensor apparatus is applicable.

According to one embodiment of the present disclosure, there is provided a nitrogen oxide based gas sensor including: a substrate provided with a beam structure having a MEMS structure: a heater disposed on the substrate: a lower electrode disposed on the heater; a solid electrolyte layer disposed on the lower electrode; an upper electrode disposed on a surface of the solid electrolyte layer facing the lower electrode and configured to introduce a measurement target gas; a cavity portion formed in the substrate: and a gas flow path disposed so as to connect the cavity portion and the lower electrode, wherein the gas sensor is configured to detect a concentration of nitrogen oxide in the measurement target gas.

According to another embodiment of the present disclosure, there is provided an oxygen pump including: a substrate provided with a beam structure having a MEMS structure; a heater disposed on the substrate; a lower electrode disposed on the heater; a solid electrolyte layer disposed on the lower electrode; an upper electrode disposed on a surface of the solid electrolyte layer facing the lower electrode and configured to introduce a measurement target gas; a cavity portion formed in the substrate: and a gas flow path disposed so as to connect the cavity portion and the lower electrode, wherein the oxygen pump is configured to pump oxygen in the measurement target gas.

According to another embodiment of the present disclosure, there is provided a gas sensor apparatus including: an enclosure including a lower substrate, an upper substrate disposed on the lower substrate, a first measurement space into which a measurement target gas is introduced via a first connection path, and a second measurement space connected to the first measurement space via a second connection path; a first oxygen pump disposed in the first measurement space and provided with a beam structure having a MEMS structure; a second oxygen pump disposed in the second measurement space and provided with a beam structure having a MEMS structure; and a nitrogen oxide based gas sensor disposed in the second measurement space and provided with a beam structure having a MEMS structure.

According to another embodiment of the present disclosure, there is provided a manufacturing method of a gas sensor apparatus, including: mounting a first oxygen pump provided with a beam structure having a MEMS structure in a first measurement space which is provided in a lower substrate or an upper substrate constituting an enclosure and into which a measurement target gas is introduced via a first connection path, and mounting a second oxygen pump provided with a beam structure having a MEMS structure in a second measurement space connected to the first measurement space via a second connection path; mounting a nitrogen oxide based gas sensor provided with a beam structure having a MEMS structure in the second measurement space; and bonding the lower substrate and the upper substrate.

According to another embodiment of the present disclosure, there is provided a sensor network system comprising the aforementioned gas sensor apparatus.

BRIEF DESCRIPTION OF DRAWINGS

FIG. 2A is a schematic configuration view showing an example of a NO sensor, and FIG. 2B is an explanatory view of the operation principle of the NO sensor, enlarging a region inside frame A in FIG. 2A.

FIG. 3 is a schematic diagram showing a V-I characteristic of an oxygen ($O_2$) pump according to the present embodiment.

FIG. 4 is a schematic diagram showing a V-I characteristic of a $NO_x$, sensor according to the present embodiment.

FIG. 13A is a schematic plan view of the gas sensor, and FIG. 13B is a schematic sectional structural view of the gas sensor taken along line II-II in FIG. 3A.

FIG. 24A shows a square lattice example, and FIG. 24B shows a triangular lattice example.

FIG. 25A shows a rectangular lattice example, and FIG. 25B shows a rhombic lattice example.

FIG. 26A is a first schematic sectional structural view. FIG. 26B is a second schematic sectional structural view. FIG. 26C is a third schematic sectional structural view. FIG. 26D is a fourth schematic sectional structural view.

FIG. 26E is a fifth schematic sectional structural view. FIG. 26F is a sixth schematic sectional structural view. FIG. 26G is a seventh schematic sectional structural view. FIG. 26H is an eighth schematic sectional structural view.

FIG. 27A is a first schematic sectional structural view. FIG. 27B is a second schematic sectional structural view. FIG. 27C is a third schematic sectional structural view. FIG. 27D is a fourth schematic sectional structural view. FIG. 27E is a fifth schematic sectional structural view. FIG. 27F is a sixth schematic sectional structural view.

DETAILED DESCRIPTION

Figure 1:
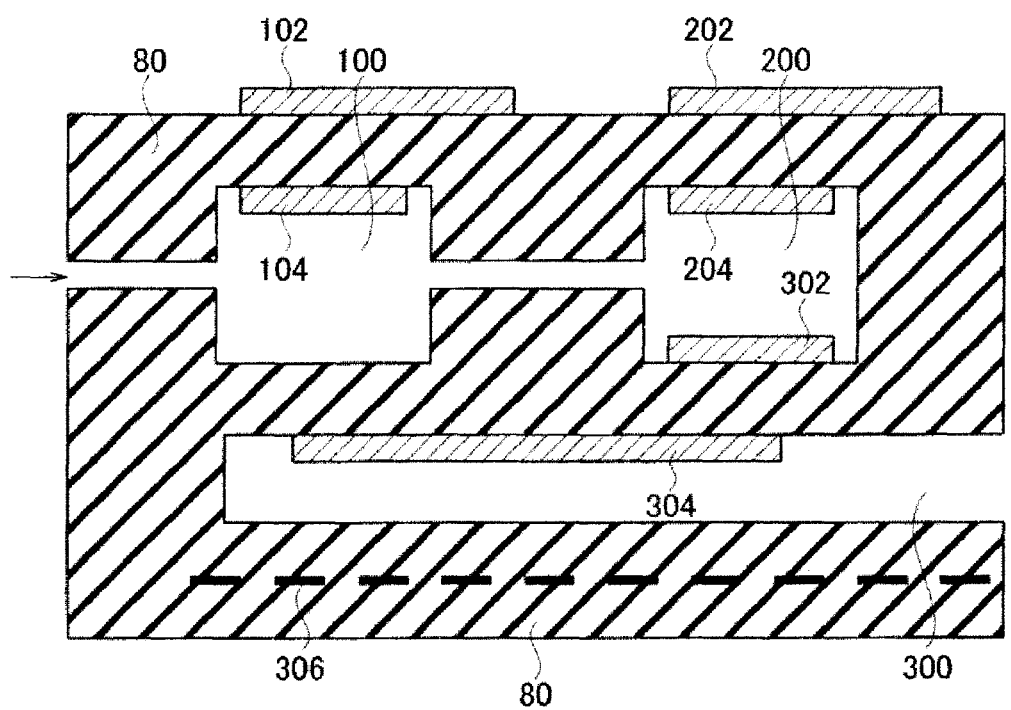
FIG. 1 is a schematic sectional structural view of a nitrogen oxide ($NO_x$ gas) sensor for a motor vehicle according to a comparative example.

Next, embodiments will be described with reference to the drawings. In the description of the drawings, the same or similar parts are designated by the same or similar reference numerals. However, it should be noted that the drawings are schematic and further that the relationship between the thickness and the plane dimension, the ratio of the thicknesses of respective layers, and the like are different from the actual ones. Therefore, specific thicknesses and dimensions should be determined with reference to the following description. In addition, it is a matter of course that the drawings also include parts having different dimensional relationships and ratios.

Furthermore, the embodiments described below exemplify apparatuses and methods for embodying the technical idea. The material, shape, structure, arrangement and the like of constituent parts are not limited to the following ones. Various modifications may be added to the respective embodiments within the scope of the claims.

In the following description of the embodiments, for the sake of convenience, the direction from the lower electrode 28D side to the upper electrode 28U side is defined as upward (upward direction), and the opposite direction is defined as downward (downward direction). Furthermore, the direction substantially parallel to the upward direction and the downward direction defined as above is referred to as a plane-perpendicular direction, and the direction substantially orthogonal to the upward direction and the downward direction defined as above is referred to as an in-plane direction.

Comparative Example

First, prior to explaining a gas sensor apparatus to which a $NO_x$ sensor according to the present embodiment is applied, an in-vehicle $NO_x$ sensor according to a comparative example will be briefly described.

As shown in FIG. 1, the in-vehicle $NO_x$ sensor according to the comparative example includes a sensor substrate (a laminated structure of zirconia solid electrolyte) 80 which takes advantage of oxygen ion conductivity of zirconia. A heater 306 is buried in the sensor substrate 80.

The sensor substrate 80 is provided with two spaces 100 and 200. In a first space 100 connected to a gas inlet port, there is disposed one of a pair of electrodes 102 and 104 (for example, the electrode 104) constituting a first oxygen pump. The other electrode 102 of the first oxygen pump is disposed on the other surface of the sensor substrate 80 opposite to the arrangement surface of the one electrode 104. In a second space 200, there are provided one of a pair of electrodes 202 and 204 (for example, the electrode 204) constituting a second oxygen pump and one of a pair of electrodes 302 and 304 (for example, the electrode 302) constituting a NO detection sensor.

The other electrode 102 of the first oxygen pump is disposed on the surface of the sensor substrate 80 opposite to the one electrode 104. The other electrode 202 of the second oxygen pump is disposed on the surface of the sensor substrate 80 opposite to the one electrode 204. The other electrode 304 constituting the NO detection sensor is disposed on the surface of the sensor substrate 80 opposite to the one electrode 302 in an air hole 300.

In the in-vehicle $NO_x$ sensor having such a configuration, the first oxygen pump removes oxygen in an exhaust gas introduced in the direction of an arrow, as a predetermined voltage is applied between the electrodes 102 and 104 ($O_2 \rightarrow$ several ppm). The second oxygen pump further removes oxygen in the exhaust gas, as a predetermined voltage is applied between the electrodes 202 and 204 ($O_2 \rightarrow 10^{-3}$ ppm). Nitrogen oxide ($NO_x$) in the exhaust gas from which oxygen has been removed by applying a predetermined voltage between the electrodes 302 and 304, is decomposed into oxygen $O_2$ and nitrogen $N_2$ ($NO \rightarrow \frac{1}{2}N_2 + \frac{1}{2}O_2$). The NO detection sensor measures the $O_2$ concentration generated during the decomposition, thereby outputting a signal proportional to the $NO_x$ concentration in the exhaust gas. Removal of oxygen $O_2$ promotes decomposition (reduction) of NO in an equilibrium reaction ($NO \leftarrow \rightarrow N_2 + O_2$).

However, in the in-vehicle $NO_x$ sensor according to the comparative example, when ammonia ($NH_3$) is contained in the exhaust gas, $NH_3$ is changed to NO due to the oxidation of combustible components in the platinum (Pt) group metal constituting the electrodes 102 and 104 of the first oxygen pump. Therefore, there is a problem that the $NO_x$ concentration in the exhaust gas cannot be correctly detected ($4NH_3 + 5O_2 \rightarrow 4NO + 6H_2O$). Accordingly, it is preferable that even when $NH_3$ is contained in the exhaust gas, the $NO_x$ concentration in the exhaust gas can be correctly detected.

The present embodiment will be described below. In the following description, Si is silicon as a semiconductor material, Pt is platinum as a porous material, Ti is Titanium as an electrode material, and YSZ is yttrium-stabilized zirconia as a solid electrolyte material.

In the present embodiment, the oxygen ($O_2$) pump 10 and the $NO_x$ sensor 20 have substantially the same configuration. A limit current type gas sensor 1, which will be described later, may be applied to both the oxygen pump 10 and the $NO_x$ sensor 20.

[Operation Principle of NO Sensor]

Figure 2A:
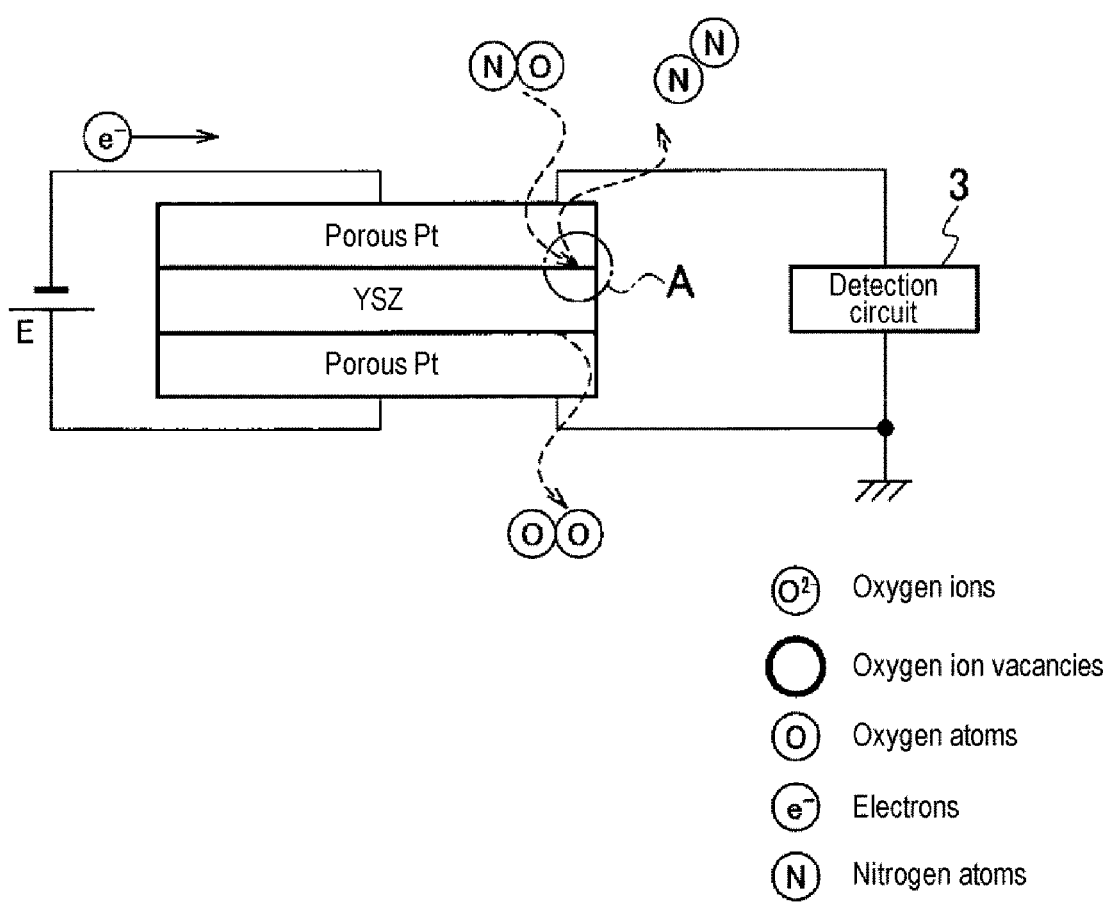
FIGS. 2A and 2B are views schematically showing the operation principle of a gas sensor apparatus to which a $NO_x$ sensor according to the present embodiment is applied.
Figure 2B:
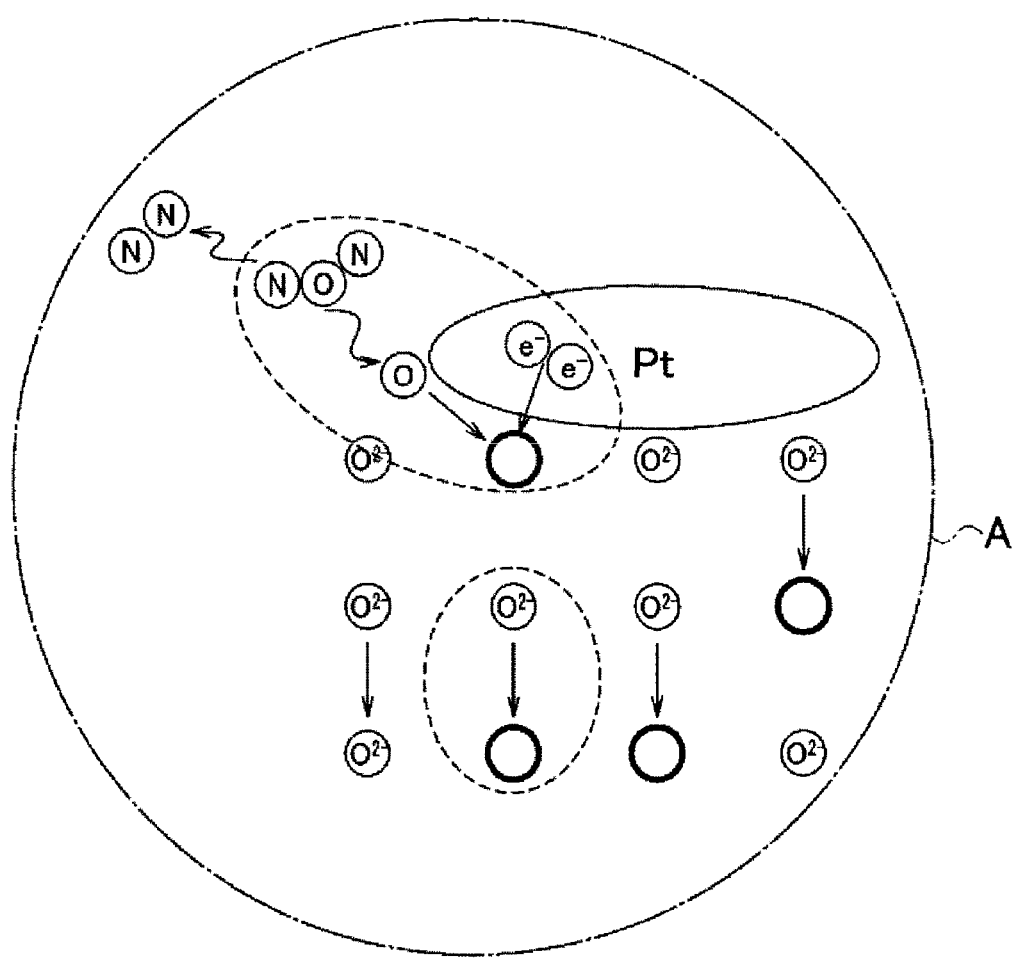

The basic structure of the NO sensor for detecting humidity (NO) is represented as shown in FIG. 2A, and the basic operation principle of the NO sensor is represented as shown in FIG. 2B.

That is to say, as shown in FIG. 2A, the NO sensor includes a lower electrode made of a porous Pt film, a solid electrolyte layer (YSZ) disposed on the lower electrode, and an upper electrode (porous Pt film) disposed on the solid electrolyte layer facing the lower electrode.

When a predetermined voltage E is applied from a power source using the lower electrode as an anode and using the upper electrode as a cathode, oxygen ionization and oxygen ion conduction occur in the NO sensor as shown in FIG. 2B.

When a voltage of, for example, 0.4 V or more is applied as the predetermined voltage E in a state in which the NO sensor is heated to about 700 degrees C., as electrons $e^-$ are supplied from the power source, nitrogen oxide $NO_x$ in the exhaust gas is decomposed into nitrogen atoms N and oxygen atoms O. The decomposed nitrogen atoms N are turned into a molecule $N_2$ and are released from, for example, the vicinity of an interface between the solid electrolyte layer and the upper electrode. The decomposed oxygen atoms O are turned into a molecule $O_2$ and are released from, for example, the vicinity of an interface between the solid electrolyte layer and the lower electrode.

In that process, in the vicinity of the interface of the solid electrolyte layer, some of the oxygen atoms O are ionized by bonding with the electrons $e^-$ to become oxygen ions $O^{2-}$ and are conducted to oxygen ion vacancies.

Since the occurrence of phenomena such as oxygen ionization and oxygen ion conduction is proportional to the concentration of NO, the limit current value of the NO sensor varies with the concentration of NO.

[I-V Characteristic of Gas Sensor]

Figure 5:
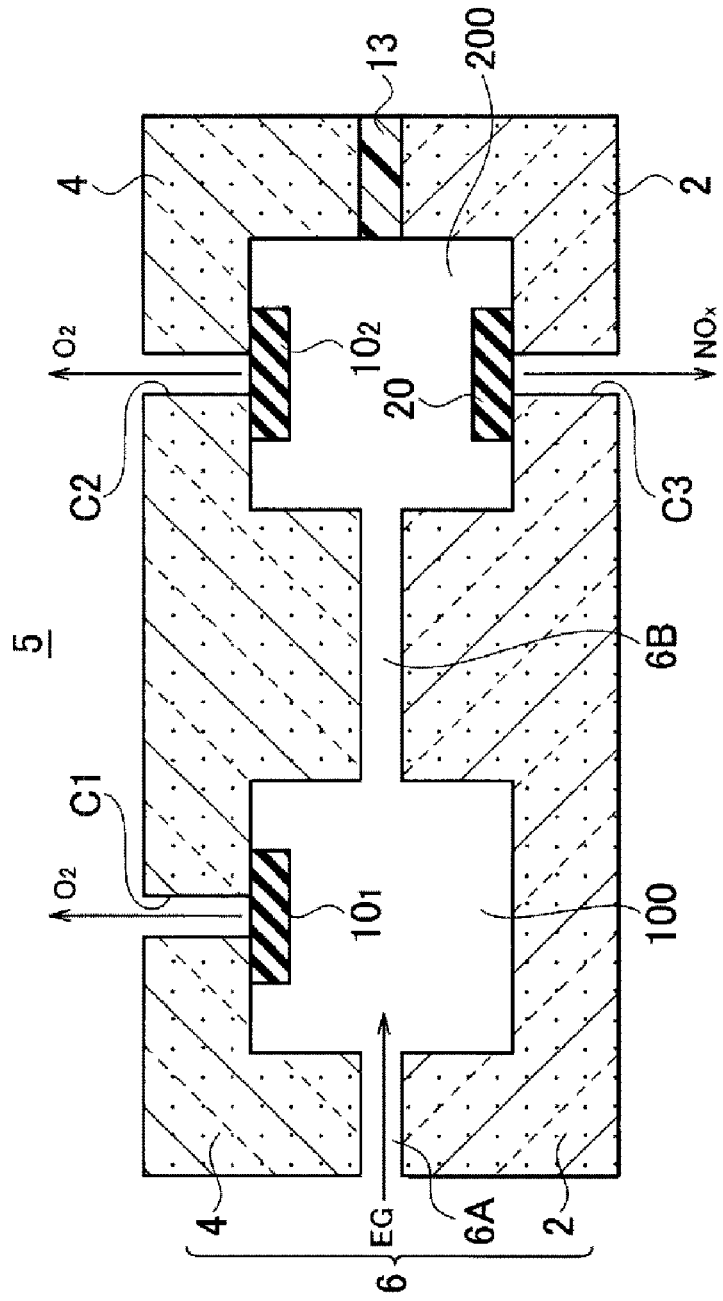
FIG. 5 is a schematic sectional structural view of a gas sensor apparatus to which a $NO_x$ sensor according to a first embodiment is applicable.

As shown in FIG. 5, a gas sensor apparatus 5 to which the $NO_x$ sensor according to the present embodiment is applicable includes oxygen pumps 10 ($10_1$ and $10_2$) for pumping oxygen in the exhaust gas (measurement target gas), and a $NO_x$ sensor 20 for detecting a $NO_x$ concentration (predetermined gas concentration) in the exhaust gas.

The I-V characteristics of the oxygen pumps $10_1$ and $10_2$ are represented as shown in FIG. 3, and the I-V characteristic of the $NO_x$ sensor 20 is represented as shown in FIG. 4.

The $NO_x$ sensor 20 detects the $NO_x$ concentration in the exhaust gas by measuring the concentration of oxygen generated due to the decomposition of NO. The $NO_x$ sensor 20 is a so-called oxygen sensor. Therefore, as is apparent from FIGS. 3 and 4, the oxygen sensor can be directly used as a $NO_x$ sensor by sufficiently lowering the oxygen concentration in the exhaust gas through pumping and by eliminating the offset amount in the current value due to the oxygen concentration.

First Embodiment

A schematic sectional structure of the gas sensor apparatus 5 to which a gas sensor according to a first embodiment is applicable is represented as shown in FIG. 5.

Specifically, as shown in FIG. 5, the gas sensor apparatus 5 to which the gas sensor according to the first embodiment is applicable includes: a sensor apparatus main body (enclosure) 6 which includes a lower substrate 2 and an upper substrate 4 disposed on the lower substrate 2 and into which an exhaust gas EG is introduced; oxygen pumps (first and second oxygen pumps) $10_1$ and $10_2$ disposed in measurement chambers (measurement spaces) 100 and 200 of a hollow structure, which are provided in the sensor apparatus main body 6 and which are formed by the lower substrate 2 and the upper substrate 4, and configured to pump oxygen in the exhaust gas EG; and a $NO_x$ sensor (gas sensor) 20 disposed in the measurement chamber 200, which is provided in the sensor apparatus main body 6 and which is formed by the lower substrate 2 and the upper substrate 4, and configured to detect a $NO_x$ concentration based on an $O_2$ concentration in the exhaust gas EG.

That is to say, the gas sensor apparatus 5 includes: the enclosure 6 including the lower substrate 2, the upper substrate 4 disposed on the lower substrate 2, the first measurement space 100 into which the measurement target gas EG is introduced via a first connection path (flow path) 6A, and the second measurement space 200 connected to the first measurement space 100 via a second connection path (flow path) 6B; the first oxygen pump $10_1$ disposed in the first measurement space 100 and provided with a beam structure having a MEMS structure; the second oxygen pump $10_2$ disposed in the second measurement space 200 and provided with a beam structure having a MEMS structure; and the nitrogen oxide based gas sensor 20 disposed in the second measurement space 200 and provided with a beam structure having a MEMS structure.

In the measurement chamber 200, the oxygen pump $10_2$ and the $NO_x$ sensor 20 are disposed on the upper substrate 4 and the lower substrate 2, respectively, so as to face each other in a plane-perpendicular direction.

The sensor apparatus main body 6 is configured such that the lower substrate 2 and the upper substrate 4 are bonded together by, for example, an adhesive layer 13. The lower substrate 2 and the upper substrate 4 may be formed by, for example, silicon (Si) substrates.

Since the Si substrates are easier to process and work than the solid electrolyte layer (YSZ film) described in the comparative example, it is easy to assemble and manufacture the gas sensor apparatus 5.

The oxygen pump $10_1$ is mounted on the upper substrate 4 in the measurement chamber 100 and is configured to remove oxygen in the exhaust gas EG guided into the measurement chamber 100 via the flow path 6A ($O_2 \rightarrow$ several ppm). The oxygen pump $10_2$ is mounted on the upper substrate 4 in the measurement chamber 200 and is configured to further remove oxygen in the exhaust gas EG guided into the measurement chamber 200 via the flow path 6B ($O_2 \rightarrow 10^{-3}$ ppm). The $O_2$ gas removed from the exhaust gas EG by the oxygen pumps $10_1$ and $10_2$ is exhausted to the outside of the sensor apparatus main body 6 from flow paths C1 and C2.

The $NO_x$ sensor 20 is mounted on the lower substrate 2 in the measurement chamber 200 and is configured to detect the $NO_x$ concentration in the exhaust gas EG in which NO decomposition (reduction) in an equilibrium reaction of $NO \leftarrow \rightarrow N_2 + O_2$ is promoted by the removal of the $O_2$ gas ($NO \rightarrow \frac{1}{2} N_2 + \frac{1}{2} O_2$). The $NO_x$ gas detected by the $NO_x$ sensor 20 is exhausted to the outside of the sensor apparatus main body 6 via a flow path C3.

As will be described in detail later, the oxygen pumps $10_1$ and $10_2$ and the $NO_x$ sensor 20 are gas sensors provided with, for example, a substrate of MEMS (Micro Electro Mechanical Systems) beam structure and have substantially the same configuration.

Since the oxygen pumps $10_1$ and $10_2$, the $NO_x$ sensor 20 and the sensor apparatus main body 6 are separately formed in the gas sensor apparatus 5, it is possible to easily change the sensitivity and the sensing accuracy of the gas sensor apparatus 5 according to the performance of the oxygen pumps $10_1$ and $10_2$ and the $NO_x$ sensor 20 to be mounted.

According to the gas sensor apparatus 5 to which the gas sensor according to the first embodiment is applicable, by adopting the Si substrate for forming the sensor apparatus main body 6, it is easy to assemble the gas sensor apparatus 5. By adopting a high performance gas sensor as the gas sensor mounted on the sensor apparatus main body 6, it is possible to easily improve the sensor sensitivity and the sensing accuracy.

Particularly, by employing the configuration in which the oxygen pump $10_2$ and the $NO_x$ sensor 20 are disposed so as to face each other in the plane-perpendicular direction in the measurement chamber 200, it is possible to reduce the size of the sensor apparatus main body 6 in the in-plane direction.

Therefore, the gas sensor apparatus 5 to which the gas sensor according to the first embodiment is applicable may be suitably adopted as, for example, an in-vehicle $NO_x$ sensor.

The measurement chambers 100 and 200 may be formed on either the lower substrate 2 or the upper substrate 4.

Second Embodiment

Figure 6:
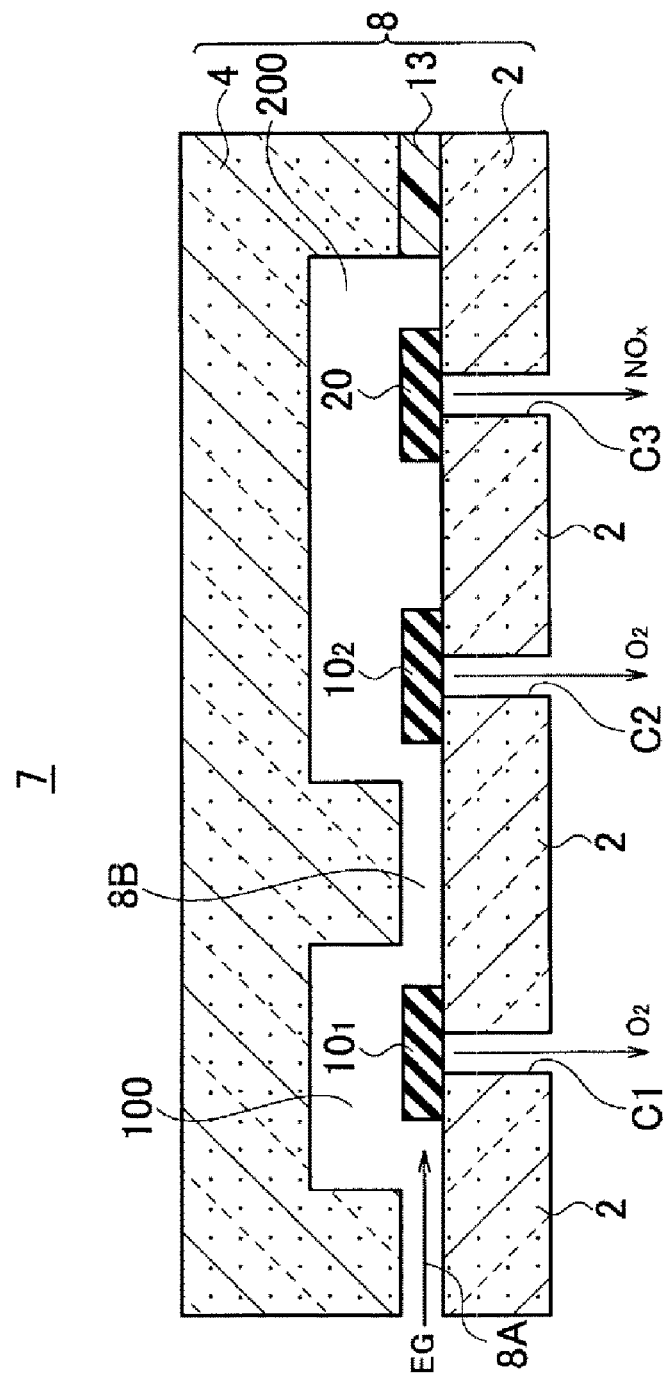
FIG. 6 is a schematic sectional structural view of a gas sensor apparatus to which a $NO_x$ sensor according to a second embodiment is applicable.

The schematic sectional structure of a gas sensor apparatus 7 to which a gas sensor according to a second embodiment is applicable is represented as shown in FIG. 6.

Specifically, as shown in FIG. 6, the gas sensor apparatus 7 to which the gas sensor according to the second embodiment is applicable includes: oxygen pumps $10_1$ and $10_2$ disposed in measurement chambers (measurement spaces) 100 and 200, which are provided in a sensor apparatus main body 8 and which are formed by an upper substrate 4, and configured to pump oxygen in an exhaust gas EG; and a $NO_x$ sensor 20 disposed in the measurement chamber 200, which is provided in the sensor apparatus main body 8 and which is formed by the upper substrate 4, and configured to detect a $NO_x$ concentration based on an $O_2$ concentration in the exhaust gas EG.

The gas sensor apparatus 7 is substantially the same as the gas sensor apparatus 5 shown in FIG. 5 except that the oxygen pumps $10_1$ and $10_2$ and the NO sensor 20 are mounted on a lower substrate 2 of the sensor apparatus main body 8.

Specifically, the oxygen pump $10_1$ is mounted on the lower substrate 2 in the measurement chamber 100 and is configured to remove oxygen in the exhaust gas EG guided into the measurement chamber 100 via a flow path 8A. The oxygen pump $10_2$ is mounted on the lower substrate 2 in the measurement chamber 200 and is configured to further remove oxygen in the exhaust gas EG guided into the measurement chamber 200 via the flow path 8B. The $O_2$ gas removed from the exhaust gas EG by the oxygen pumps $10_1$ and $10_2$ is exhausted to the outside of the sensor apparatus main body 8 from flow paths C1 and C2.

The $NO_x$ sensor 20 is mounted on the lower substrate 2 in the measurement chamber 200 and is configured to detect the $NO_x$ concentration in the exhaust gas EG from which the $O_2$ gas has been removed. The $NO_x$ gas detected by the $NO_x$ sensor 20 is exhausted to the outside of the sensor apparatus main body 8 via a flow path C3.

As described above, in the case of the gas sensor apparatus 7 to which the gas sensor according to the second embodiment is applicable, in the measurement chamber 200, the oxygen pump $10_2$ and the $NO_x$ sensor 20 are disposed on the lower substrate 2 so as to be adjacent to each other in the in-plane direction.

The same effects as those of the gas sensor apparatus 5 to which the gas sensor according to the first embodiment is applicable can also be expected by the gas sensor apparatus 7 to which the gas sensor according to the second embodiment having such a configuration is applicable.

Particularly, by employing the configuration in which the oxygen pump $10_2$ and the NO sensor 20 are disposed so as to be adjacent to each other in the in-plane direction in the measurement chamber 200, it is possible to reduce the size of the sensor apparatus main body 8 in the plane-perpendicular direction.

It may be possible to employ a configuration in which the measurement chambers 100 and 200 are formed on the lower substrate 2. It may be possible to employ a configuration in which the oxygen pumps $10_1$ and $10_2$ and the $NO_x$ sensor 20 are mounted on the upper substrate 4.

(Manufacturing Process)

A manufacturing process will be described using the gas sensor apparatus 7 shown in FIG. 6 as an example.

An example of a manufacturing process of the gas sensor apparatus 7 to which the gas sensor according to the second embodiment is applicable is shown in FIGS. 7 to 12.

Figure 7:
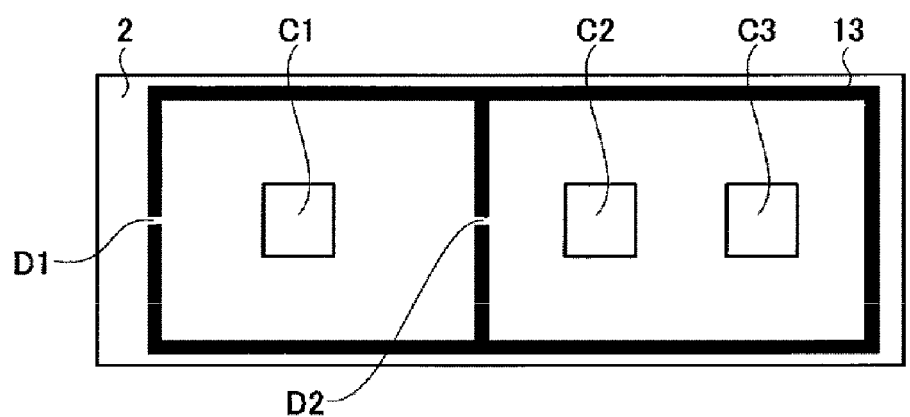
FIG. 7 is a schematic plan view showing one step of a manufacturing process of the gas sensor apparatus shown in FIG. 6 as an example.

When manufacturing the gas sensor apparatus 7, first, as shown in FIG. 7, the lower substrate 2 constituting the sensor apparatus main body 8 is prepared. On the lower substrate 2, for example, the flow paths C1, C2 and C3 are formed in a corresponding relationship with the measurement chambers 100 and 200 to be formed on the upper substrate 4.

Further, on the lower substrate 2, the adhesive layer 13 is coated on the lower substrate 2 so as to surround the measurement chambers 100 and 200. Cutout portions D1 and D2 on which an adhesive is not coated are provided in the adhesive layer 13 in a corresponding relationship with the flow path 8A.

Figure 8:
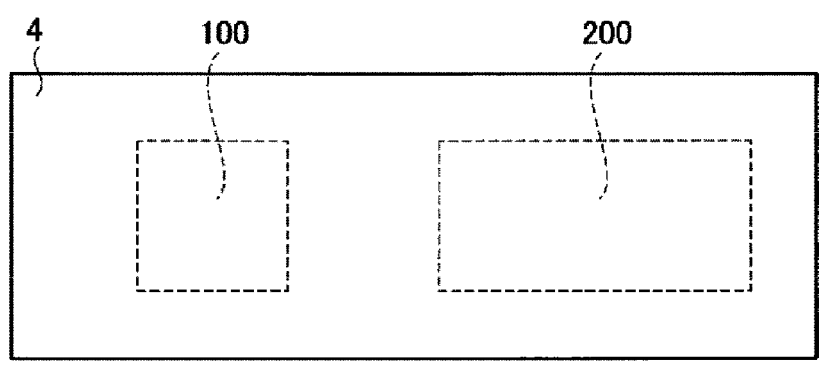
FIG. 8 is a schematic plan view showing one step of a manufacturing process of the gas sensor apparatus shown in FIG. 6 as an example.

Similarly, when manufacturing the gas sensor apparatus 7, as shown in FIG. 8, the upper substrate 4 constituting the sensor apparatus main body 8 is prepared. The oxygen pumps 10 and $10_2$ and the $NO_x$ sensor 20 are mounted on the measurement chambers 100 and 200 which are formed on the upper substrate 4.

Figure 9:
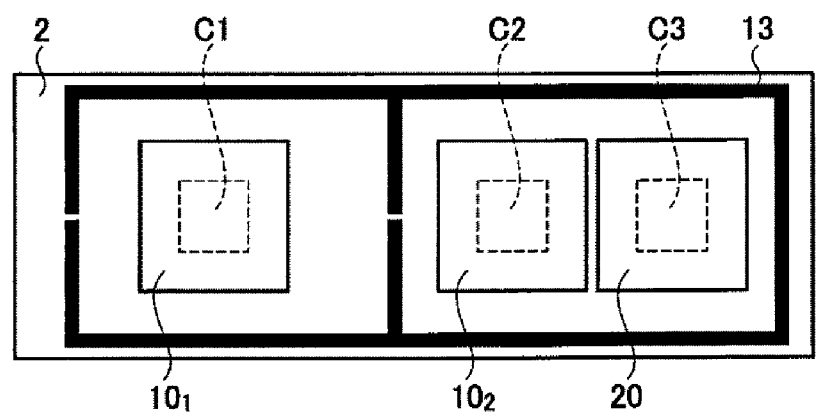
FIG. 9 is a schematic plan view showing one step of a manufacturing process of the gas sensor apparatus shown in FIG. 6 as an example.

FIG. 9 shows a state in which the oxygen pumps $10_1$ and $10_2$ and the $NO_x$ sensor 20 are separately formed and are mounted on the lower substrate 2 prepared in advance.

Figure 10:
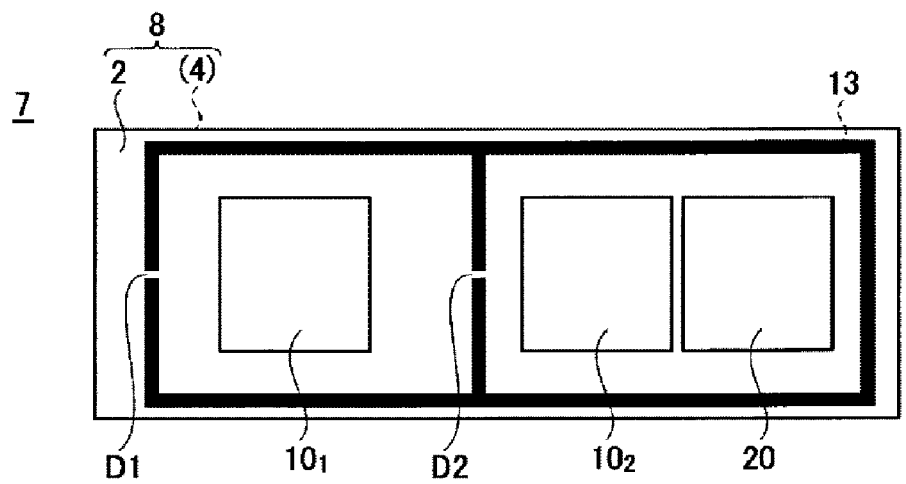
FIG. 10 is a schematic plan view showing one step of a manufacturing process of the gas sensor apparatus shown in FIG. 6 as an example.

Furthermore, FIG. 10 shows a state in which the upper substrate 4 is bonded onto the lower substrate 2 on which the oxygen pumps $10_1$ and $10_2$ and the $NO_x$ sensor 20 are mounted. In FIG. 10, the gas sensor apparatus 7 is shown in a state of being seen through the upper substrate 4.

Figure 11:
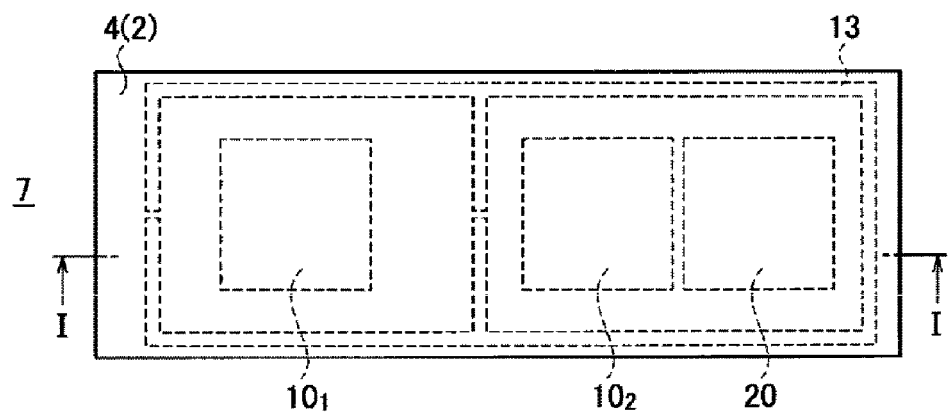
FIG. 11 is a schematic plan view showing one step of a manufacturing process of the gas sensor apparatus shown in FIG. 6 as an example.
Figure 12:
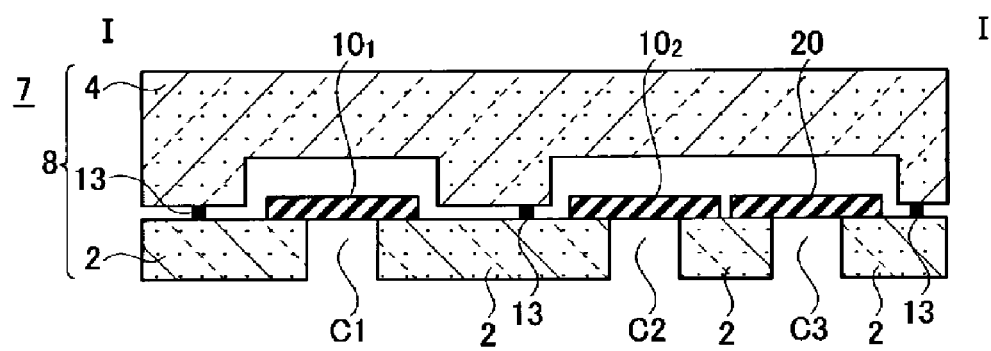
FIG. 12 is a view showing one step of a manufacturing process of the gas sensor apparatus shown in FIG. 6 as an example and is a schematic sectional structural view taken along line I-I in FIG. 11.

A schematic planar pattern configuration of the gas sensor apparatus 7 assembled in this manner is represented as shown in FIG. 11. A schematic sectional structure taken along line I-I in FIG. 11 is represented as shown in FIG. 12.

Through the above process, the gas sensor apparatus 7 on which the gas sensor according to the second embodiment is mounted is completed.

That is to say, the method of manufacturing the gas sensor apparatus 7 includes: a step of mounting the first oxygen pump $10_1$ provided with a beam structure having a MEMS structure in the first measurement space 100 which is provided in the lower substrate 2 or the upper substrate 4 constituting the enclosure 8 and into which the measurement target gas EG is introduced via the first connection path (flow path) 8A, and mounting the second oxygen pump $10_2$ provided with a beam structure having a MEMS structure in the second measurement space 200 connected to the first measurement space 100 via the second connection path (flow path) 8B; a step of mounting the nitrogen oxide based gas sensor 20 provided with a beam structure having a MEMS structure in the second measurement space 200; and a step of bonding the lower substrate 2 and the upper substrate 4.

In the manufacture of the gas sensor apparatus 7, it is easy to change the performance of the gas sensor to be mounted or to change the layout of the lower substrate 2 and the upper substrate 4 according to the required accuracy of detection of the $NO_x$ gas or the like. Thus, the degree of freedom is high.

Specific Example of Gas Sensor

Figure 13A:
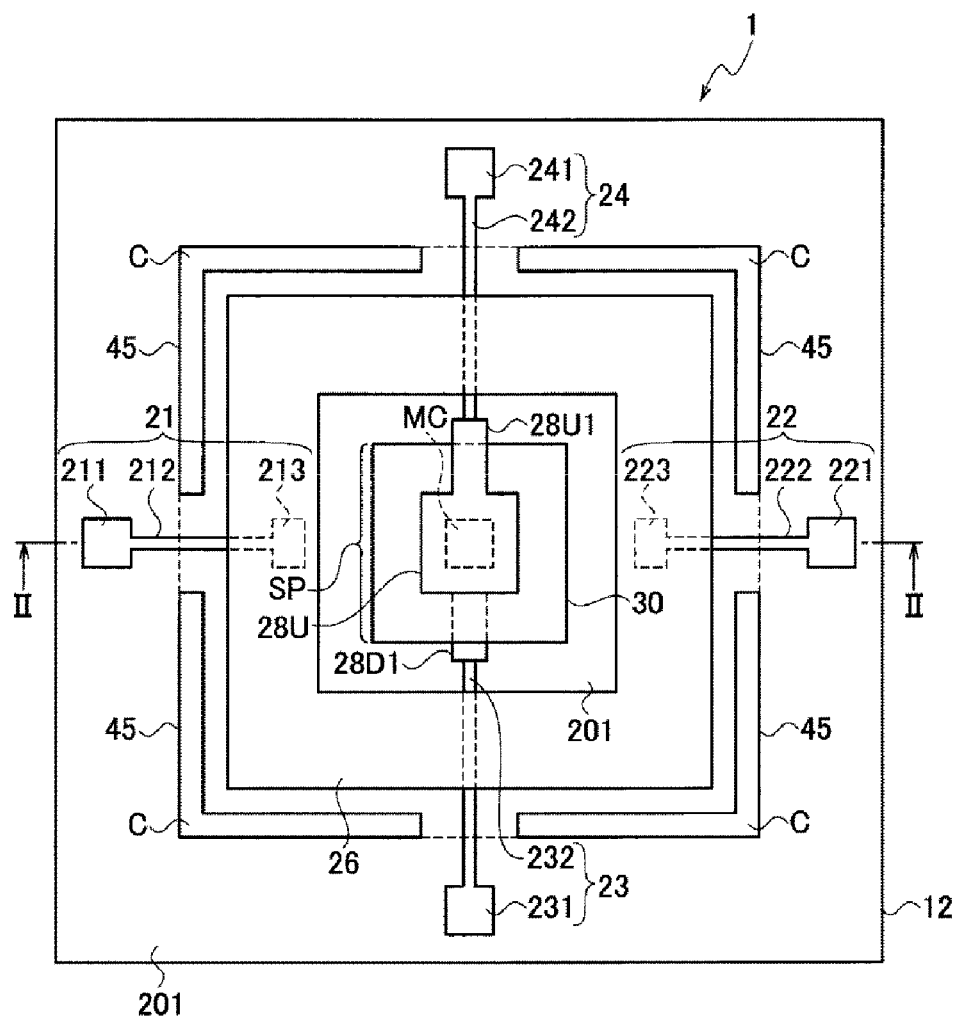
FIGS. 13A and 13B are views showing a configuration example of a limit current type gas sensor applicable as a $NO_x$ sensor according to the present embodiment.
Figure 13B:
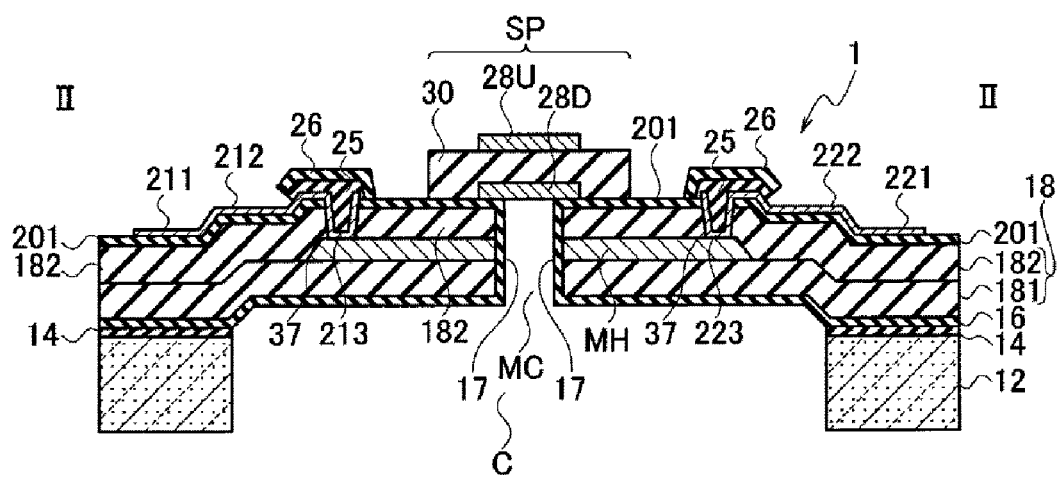

A schematic planar pattern configuration of the gas sensor 1 according to the present embodiment is represented as shown in FIG. 13A, and a schematic sectional structure of the gas sensor 1 taken along line II-II in FIG. 13A is represented as shown in FIG. 13B.

In the present embodiment, the oxygen pump 10 and the $NO_x$ sensor 20 have substantially the same configuration, and the gas sensor 1 can be applied to both the oxygen pump 10 and the $NO_x$ sensor 20.

First, the outline of the configuration will be described. As shown in FIGS. 13A and 13B, the gas sensor 1 according to the present embodiment includes a micro heater (first and second heaters) MH, a sensor portion (first and second sensor portions) SP, heater connecting portions 21 and 22, terminal electrode connecting portions 23 and 24, and a gas flow path (first and second gas flow paths) MC, and the like, which are provided on a substrate 12 having a MEMS beam structure.

The sensor portion SP includes a lower electrode 28D arranged on a membrane (having a perforated diaphragm structure) on the substrate 12, a solid electrolyte layer 30 disposed so as to cover the lower electrode 28D, and an upper electrode 28U disposed on the solid electrolyte layer 30 facing the lower electrode 28D.

In the case of the oxygen pump 10, the lower electrode 28D can be formed with a thickness of about 100 nm, for example, by a Pt/Ti electrode which is a laminated film of a Pt film and a Ti film. The Ti film is used to make the bonding with the solid electrolyte layer 30 dense and stronger. The upper electrode 28U is formed of, for example, a Pt—Au film. By driving the upper electrode 28U formed of a Pt—Au film at a low voltage using a drive voltage of approximately 0.1 to 0.2 V, for example, in a state in which the upper electrode 28U is heated to about 700 degrees C., it is possible to suppress decomposition of NO in the exhaust gas EG.

The solid electrolyte layer 30 can be formed of, for example, a YSZ film having a thickness of about 1 µm. This is because conduction between the upper and lower electrodes 28U and 28D occurs if the thickness is small. For example, the solid electrolyte layer 30 is disposed so as to cover the periphery of the lower electrode 28D, whereby conduction between the upper and lower electrodes 28U and 28D is prevented.

Since the substrate 12 has a rectangular shape in a plan view, the lower electrode 28D, the solid electrolyte layer 30 and the upper electrode 28U of the sensor portion SP may have a rectangular shape or other shapes. It is desirable that the lower electrode 28D, the solid electrolyte layer 30 and the upper electrode 28U constituting the sensor portion SP are disposed at the center of the substrate 12 in an eccentricity-free state. However, the lower electrode 28D, the solid electrolyte layer 30 and the upper electrode 28U may be disposed in an eccentric state with respect to the micro heater MH.

In a plan view, the heater connecting portions 21 and 22 are arranged so as to face each other in the in-plane direction along the cross section of FIG. 13B using the sensor portion SP as a center. The heater connecting portion 21 includes a connecting pad 211, a wiring portion 212, and a terminal portion 213. The heater connecting portion 22 includes a connecting pad 221, a wiring portion 222, and a terminal portion 223.

The terminal electrode connecting portions 23 and 24 are disposed so as to face each other in the in-plane direction orthogonal to the heater connecting portions 21 and 22 using the sensor portion SP as a center. The terminal electrode connecting portion 23 includes a connecting pad (detection terminal) 231 and a wiring portion 232. The terminal electrode connecting portion 24 includes a connecting pad (detection terminal) 241 and a wiring portion 242.

The heater connecting portions 21 and 22 and the terminal electrode connecting portions 23 and 24 are provided on an SiN film 201 and may be formed of, for example, a laminated film (Pt/Ti laminated film) of a Ti film having a thickness of 20 nm and a Pt film having a thickness of 100 nm.

The terminal portions 213 and 223 of the heater connecting portions 21 and 22 are connected to the micro heater MH. The wiring portion 232 of the terminal electrode connecting portion 23 extends in the direction of the sensor portion SP and is connected to an extension end 28D1 of the lower electrode 28D. The wiring portion 242 of the terminal electrode connecting portion 24 extends in the direction of the sensor portion SP and is connected to the extension end 28U1 of the upper electrode 28U.

A detection circuit 3 for detecting a predetermined gas concentration in a measurement target gas in a limit current manner is connected to the connecting pads 231 and 241 of the terminal electrode connecting portions 23 and 24. As will be described in detail later, by supplying a predetermined voltage to the upper electrode 28U and the lower electrode 28D of the solid electrolyte layer 30, it is possible for the detection circuit 3 to detect a concentration of oxygen contained in an exhaust gas based on a limit current.

In a plan view, the terminal portions 213 and 223 of the heater connecting portions 21 and 22 are covered with a SiN film 26 disposed so as to surround the outer peripheral portion of the sensor portion SP. A $SiO_2$ film 25 is buried between the SiN film 26 and the terminal portions 213 and 223.

In a plan view, L-shaped opening portions 45 are respectively disposed on the outer side of the SiN film 26 and in the boundary portions between an active region and a non-active region corresponding to the respective corners of the substrate 12 except for the heater connecting portions 21 and 22 and the terminal electrode connecting portions 23 and 24. The opening portions 45 are opened at the time of forming a cavity portion C as first and second cavity portions. The opening portions 45 may have a shape other than an L shape, for example, a straight shape (I shape) or the like.

The micro heater MH is provided between $SiO_2$ films 181 and 182 constituting an insulating layer 18. The micro heater MH is, for example, a polysilicon layer (polysilicon heater) having a thickness of 0.2 μm. B (boron) which is a p-type impurity is implanted into the polysilicon layer at a high concentration (for example, $4 \times 10^{19}$ $cm^{-3}$) so that a resistance value is about 300Ω. The thermal conductivity of the micro heater MH is preferably, for example, about 80 W/mK. In addition, for example, the micro heater MH is preferably disposed below the solid electrolyte layer 30 so as to have a rectangular shape and is preferably formed so as to have a larger area than the solid electrolyte layer 30.

The micro heater MH is used to heat the solid electrolyte layer 30. For example, the micro heater MH is supplied with a predetermined voltage which is applied from the terminal portions 213 and 223 formed in opening portions 37 opened in the SiN film 201 and the $SiO_2$ film 182 to the connecting pads 211 and 221 via the wiring sections 212 and 222.

The micro heater MH is not limited to being disposed between the $SiO_2$ films 181 and 182 on the substrate 12 but may be disposed under the substrate 12 or embedded in the substrate 12. Alternatively, it may be possible to employ a configuration in which a laminated film (not shown) of a $SiO_2$ film and a SiN film, which contains a micro-heater MH made of polysilicon, is formed on the surface of the substrate 12. In addition, the micro heater MH may also be configured by a Pt heater or the like formed by printing.

Depending on the size (scale) of the gas sensor 1, instead of the micro heater MH, a nano-sized heater may also be used as long as it has a larger area than the sensor portion SP.

In the sectional structure of FIG. 13B with the sensor portion SP directed upward, the cavity portion C of an open type structure connected to the opening portions 45 and disposed so that the substrate 12 surrounds the sensor portion SP is formed in the substrate 12 under the micro heater MH. An insulating layer 16 made of a SiON film is provided at the interface between the cavity portion C and the $SiO_2$ film 181 corresponding to the cavity portion C. The insulating layer 16 and an insulating layer 14 made of a $SiO_2$ film are provided at the interface between the substrate 12 and the $SiO_2$ film 181.

The substrate 12 of a MEMS beam structure has a thickness of, for example, about 10 μm and is formed so that the cavity portion C is substantially larger than the micro heater MH, thereby preventing escape of heat from the membrane. Although the plan-view shape of the cavity portion C is not particularly limited, it is desirable to form the cavity portion C in a square shape just like the sensor portion SP and the micro heater MH.

The gas flow path MC connected to the cavity portion C of the substrate 12 is provided in the membrane corresponding to the sensor portion SP so that the measurement target gas introduced from the side of the upper electrode 28U is exhausted to the side of the cavity portion C. The flow path diameter of the gas flow path MC is, for example, several μm.

A structure in which the micro heater MH is sandwiched by the insulating layer 16 and the SiN film 201 and embedded between the $SiO_2$ films 181 and 182 will be referred to as a membrane. In particular, a membrane having the gas flow path MC will be referred to as a perforated diaphragm structure. The wall surface of the gas flow path MC is covered with an insulating layer 16 and an insulating layer (for example, a SiN film) 17 connected to the SiN film 201.

As the MEMS beam structure, it may be possible to adopt a structure in which the cavity portion C is formed by bonding the substrate 12. Therefore, the substrate 12 is not limited to Si. An epoxy resin, ceramics or the like may also be used.

That is to say, the nitrogen oxide based gas sensor 20 according to the present embodiment includes the substrate 12 provided with a beam structure having a MEMS structure, the heater MH disposed on the substrate 12, the lower electrode 28D disposed on the heater MH, the solid electrolyte layer 30 disposed on the lower electrode 28D, the upper electrode 28U disposed on a surface of the solid electrolyte layer 30 facing the lower electrode 28D and configured to introduce a measurement target gas, the cavity portion C formed in the substrate 12, and the gas flow path MC disposed to connect the cavity portion C and the lower electrode 28D. The nitrogen oxide based gas sensor 20 detects the concentration of nitrogen oxide in the measurement target gas.

Figure 14:
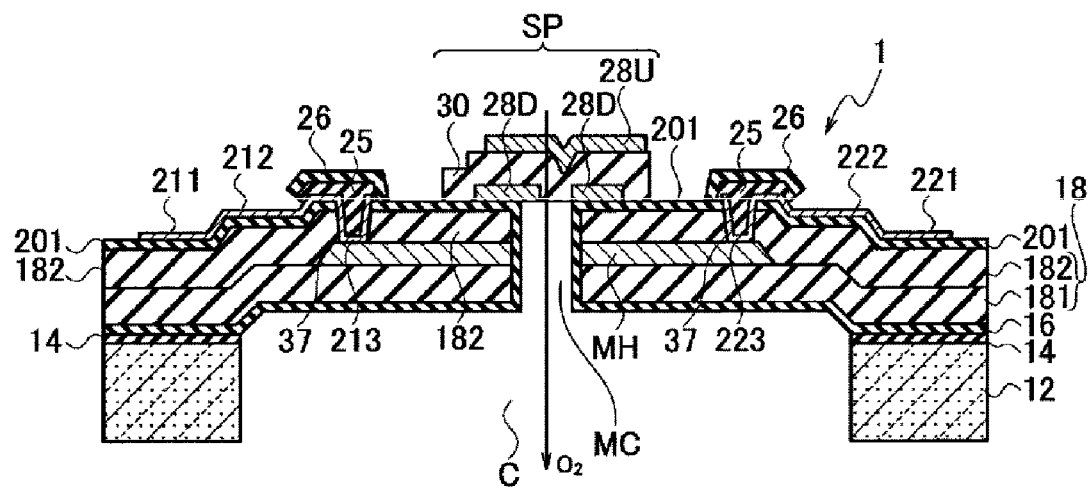
FIG. 14 is a schematic sectional structural view showing another configuration example of the limit current type gas sensor shown in FIGS. 13A and 13B.
Figure 15:
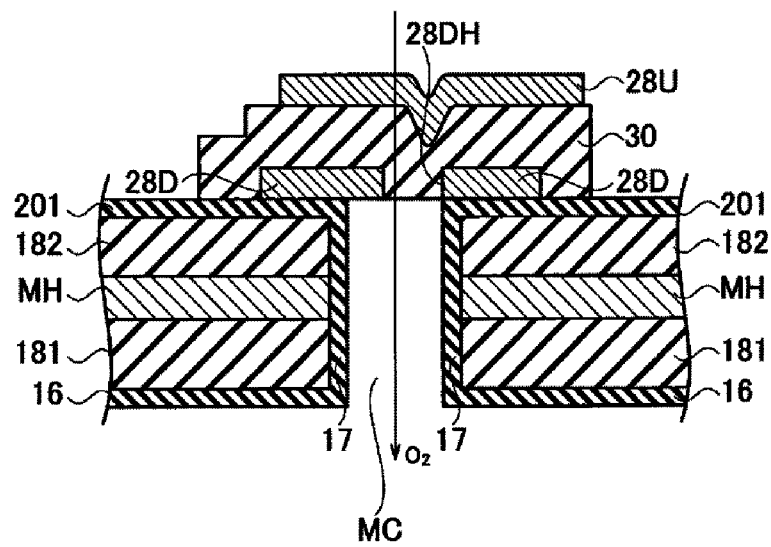
FIG. 15 is a schematic sectional structural view enlarging the main part of the limit current type gas sensor shown in FIG. 14.

As shown in FIGS. 14 and 15, the lower electrode 28D may be provided with an opening portion 28DH connected to the gas flow path MC.

As shown in FIGS. 14 and 15, the gas sensor 1 applicable as the oxygen pump 10 includes the substrate 12 having an MEMS beam structure in which the cavity portion C has an open type structure. The gas sensor 1 is configured to introduce an exhaust gas into the solid electrolyte layer 30 via the upper electrode 28U as the micro heater MH performs heating. The gas sensor 1 is configured to take out the O$_2$ gas contained in the exhaust gas introduced into the solid electrolyte layer 30 and to exhaust the O$_2$ gas from the opening portion 28DH of the lower electrode 28D through the gas flow path MC.

In the oxygen pump 10, the introduction of a gas into the solid electrolyte layer 30 may be accompanied by a suction operation.

That is to say, the oxygen pump 10 according to the present embodiment includes the substrate 12 provided with a beam structure having a MEMS structure, the heater MH disposed on the substrate 12, the lower electrode 28D disposed on the heater MH, the solid electrolyte layer 30 disposed on the lower electrode 28D, the upper electrode 28U disposed on a surface of the solid electrolyte layer 30 facing the lower electrode 28D and configured to introduce a measurement target gas, the cavity portion C formed in the substrate 12, and the gas flow path MC disposed so as to connect the cavity portion C and the lower electrode 28D. The oxygen pump 10 pumps oxygen in the measurement target gas.

On the other hand, in the case of the gas sensor 1 applicable as the NO$_x$ sensor 20, the lower electrode (second lower electrode) 28D can be formed with a thickness of about 100 nm by, for example, a Pt/Ti electrode which is a laminated film of a Pt film and a Ti film. The upper electrode (second upper electrode) 28U is formed by, for example, a Pt film. By driving the upper electrode 28U formed of a Pt film at a low voltage using a drive voltage of approximately 0.4 to 0.8 V, for example, in a state in which the upper electrode 28U is heated to about 700 degrees C., it is possible to promote decomposition of NO in the exhaust gas EG.

As shown in FIGS. 14 and 15, the gas sensor 1 applicable as the NO$_x$ sensor 20 includes the substrate 12 having an MEMS beam structure in which the cavity portion C has an open type structure. The gas sensor 1 is configured to introduce an exhaust gas into the solid electrolyte layer 30 via the upper electrode 28U as the micro heater MH performs heating. The gas sensor 1 is configured to take out the NO$_x$ gas contained in the exhaust gas introduced into the solid electrolyte layer 30 and to exhaust the NO$_x$ gas from the opening portion 28DH of the lower electrode 28D through the gas flow path MC.

In the NO$_x$ sensor 20, the introduction of a gas into the solid electrolyte layer 30 may be accompanied by a suction operation.

Although the gas sensor 1 according to the present embodiment is accompanied by the heating of the micro heater MH, by using the beam structure (open type structure) having a MEMS structure as a basic structure, it is possible to reduce the heat capacity of the sensor portion SP, thereby improving the sensor sensitivity.

Next, a method of forming the sensor portion SP of the gas sensor 1 will be described.

For example, a method of forming the sensor portion SP of the gas sensor 1 in which the membrane has a perforated diaphragm structure as shown in FIG. 15 is shown in FIGS. 16 to 19.

Figure 16:
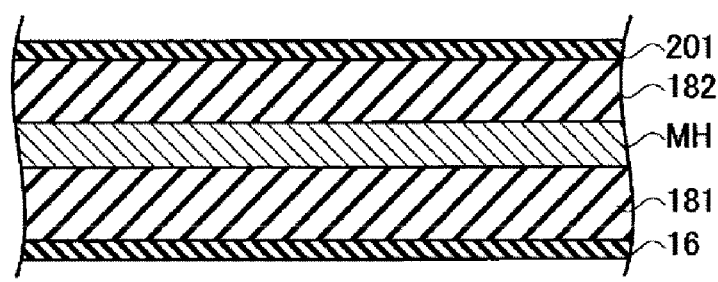
FIG. 16 is a schematic plan view showing a method of forming the main part of the limit current type gas sensor shown in FIG. 15.

(a) First, as shown in FIG. 16, an insulating layer 16 made of a SiON film having a thickness of about 0.5 μm is formed on the upper surface of a substrate 12 by a plasma CVD (P-CVD) method or the like. Thereafter, a SiO$_2$ film 181 having a thickness of about 0.5 μm is formed on the insulating layer 16 by a CVD method or the like. Next, a polysilicon layer having a thickness of about 0.2 μm is formed on the upper surface of the SiO$_2$ film 181 by a low-pressure CVD method or the like. The polysilicon layer is patterned by etching or the like to form a micro heater MH. Subsequently, a SiO$_2$ film 182 having a thickness of about 0.5 μm is formed on the entire surface by a P-CVD method or the like. Then, a SiN film 201 having a thickness of about 0.5 μm is formed on the SiO$_2$ film 182, thereby forming a membrane.

Figure 17:
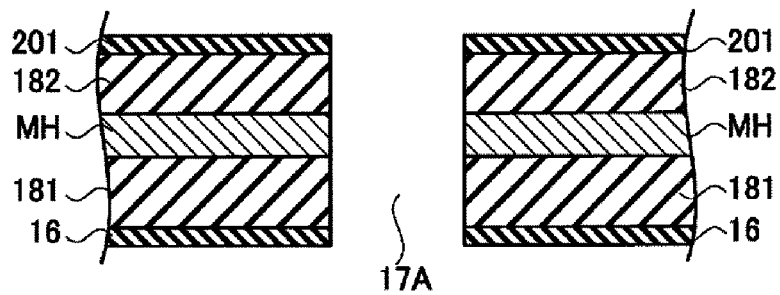
FIG. 17 is a schematic plan view showing a method of forming the main part of the limit current type gas sensor shown in FIG. 15.

(b) Thereafter, as shown in FIG. 17, a part of the membrane is selectively etched to form a through-hole 17A.

Figure 18:
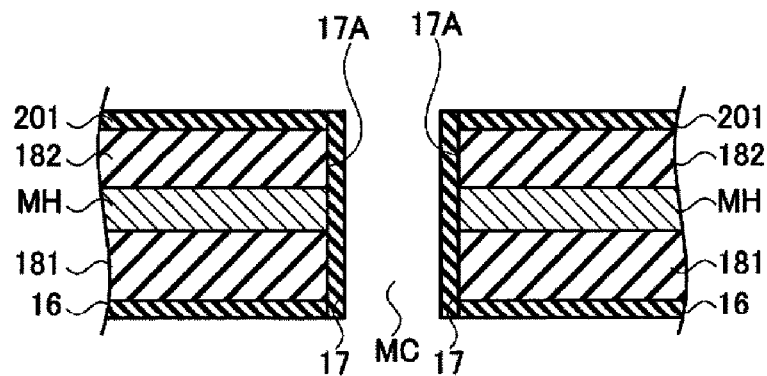
FIG. 18 is a schematic plan view showing a method of forming the main part of the limit current type gas sensor shown in FIG. 15.

(c) Then, as shown in FIG. 18, an insulating layer 17 connected to the insulating layer 16 and the SiN film 201 are formed on the wall surface of the through-hole 17A by a P-CVD method or the like, thereby coating the wall surface of a gas flow path MC.

Figure 19:
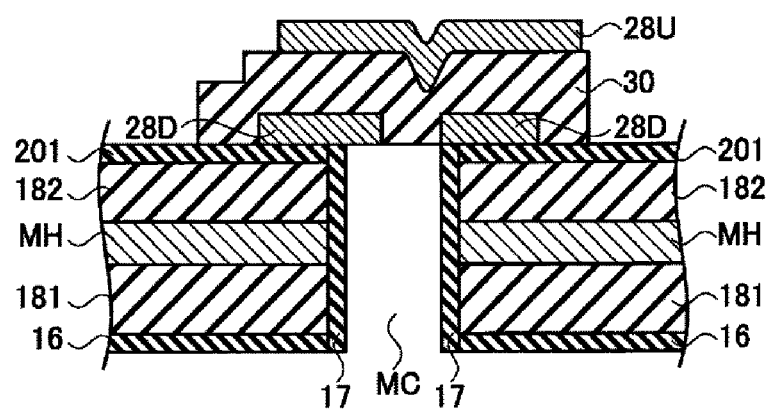
FIG. 19 is a schematic plan view showing a method of forming the main part of the limit current type gas sensor shown in FIG. 15.

(d) Thereafter, as shown in FIG. 19, a lower electrode 28D having a thickness of about 100 nm is formed on the SiN film 201 by a sputtering method or the like. An extension end 28D1 of the lower electrode 28D is connected to a wiring portion 232 of a terminal electrode connecting portion 23. Then, a solid electrolyte layer 30 made of a YSZ film is formed with a thickness of about 1 μm by a sputtering method so as to cover the lower electrode 28D. Subsequently, an upper electrode 28U having a thickness of about 100 nm is formed on the surface of the solid electrolyte layer 30 facing the lower electrode 28D. An extension end 28U1 of the upper electrode 28U is connected to a wiring portion 242 of a terminal electrode connecting portion 24.

Next, a mounting method of the oxygen pump 10 and the NO$_x$ sensor 20 will be described.

Figure 20:
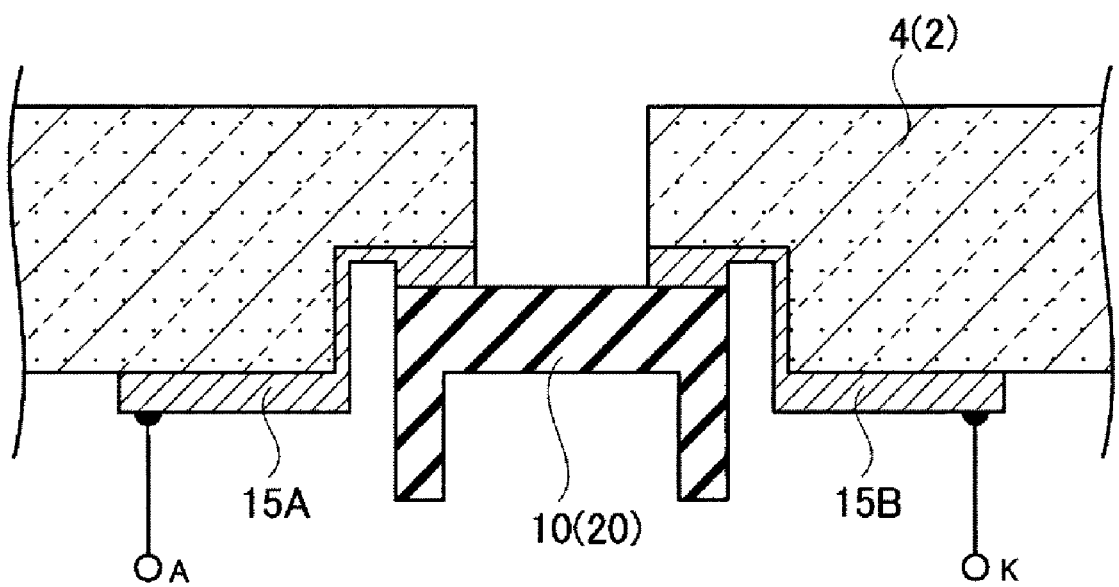
FIG. 20 is a schematic sectional structural view showing a mounting example of the $NO_x$ sensor according to the embodiment.

In a first mounting method, as shown in FIG. 20, an electrode (not shown) of an oxygen pump 10 or a NO$_x$ sensor 20 is placed to face an electrode (not shown) of a lower substrate 2 or an upper substrate 4. In this state, both electrodes are connected by using wiring layers 15A and 15B or the like. In the case of this method, the oxygen pump 10 and the NO$_x$ sensor 20 are always mounted in such a direction that the side on which the electrode is formed faces the lower substrate 2 or the upper substrate 4.

Figure 21:
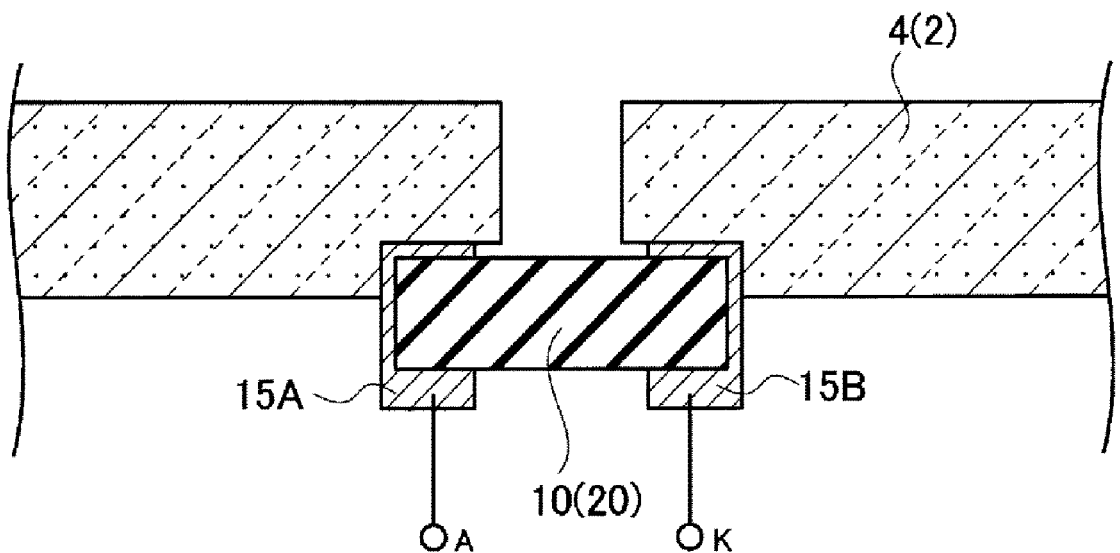
FIG. 21 is a schematic sectional structural view showing another mounting example of the $NO_x$ sensor according to the present embodiment.

In a second mounting method, as shown in FIG. 21, an electrode (not shown) of an oxygen pump 10 or a NO$_x$ sensor 20 is placed to oppose an electrode (not shown) of a lower substrate 2 or an upper substrate 4. In this state, both electrodes are connected by using wiring layers 15A and 15B or the like (flip chip method). In the case of this method, the oxygen pump 10 and the NO$_x$ sensor 20 are always mounted in such a direction that the side on which the electrode is formed opposes the lower substrate 2 or the upper substrate 4.

(First Modification)

Figure 22:
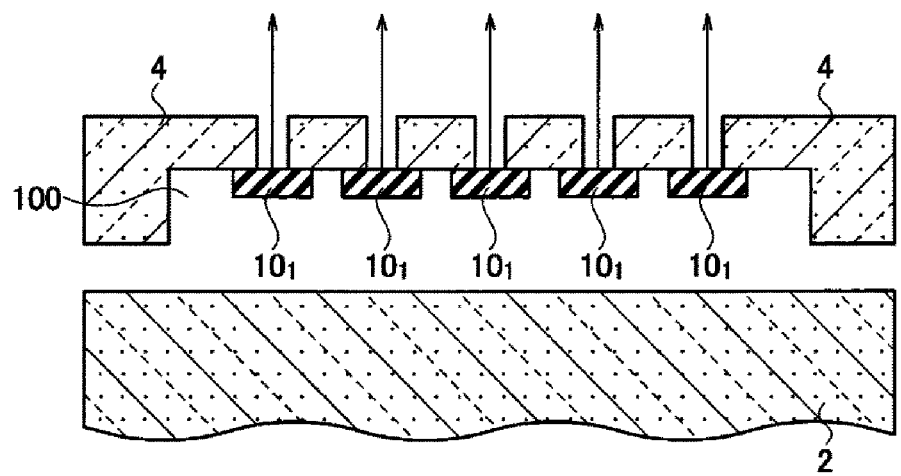
FIG. 22 is a schematic sectional structural view of a gas sensor apparatus capable of mounting a $NO_x$ sensor according to a first modification of the present embodiment.

FIG. 22 shows a first modification of the gas sensor apparatus 7 shown in FIG. 6. The first modification is an example in which, for example, five oxygen pumps 10$_1$ are mounted in one measurement chamber 100.

That is to say, according to a gas sensor apparatus 7A of the first modification, it is possible to mount a plurality of oxygen pumps 10$_1$ in one measurement chamber 100.

(Second Modification)

Figure 23:
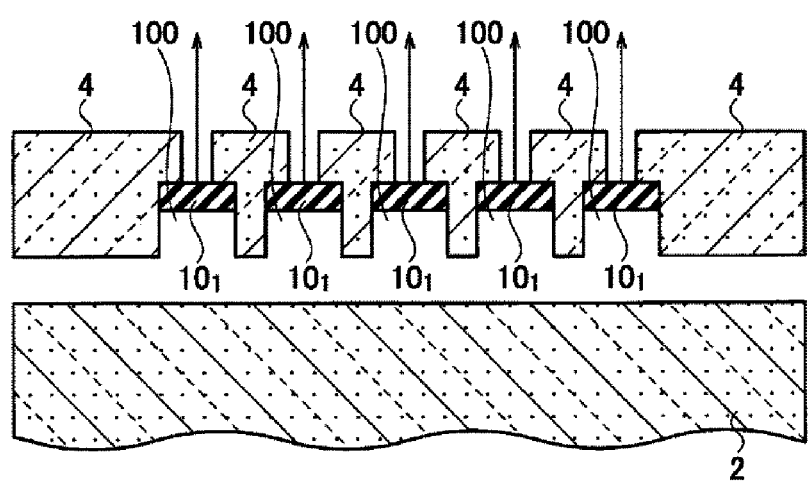
FIG. 23 is a schematic sectional structural view of a gas sensor apparatus capable of mounting a $NO_x$ sensor according to a second modification of the present embodiment.

FIG. 23 shows a second modification of the gas sensor apparatus 7 shown in FIG. 6. The second modification is an example in which, for example, oxygen pumps 10$_1$ are individually mounted in five measurement chambers 100.

That is to say, even in the case of a gas sensor apparatus 7B according to the second modification, it is possible to mount a plurality of oxygen pumps 10$_1$ with high yield.

Other Mounting Example of Gas Sensor

Figure 24A:
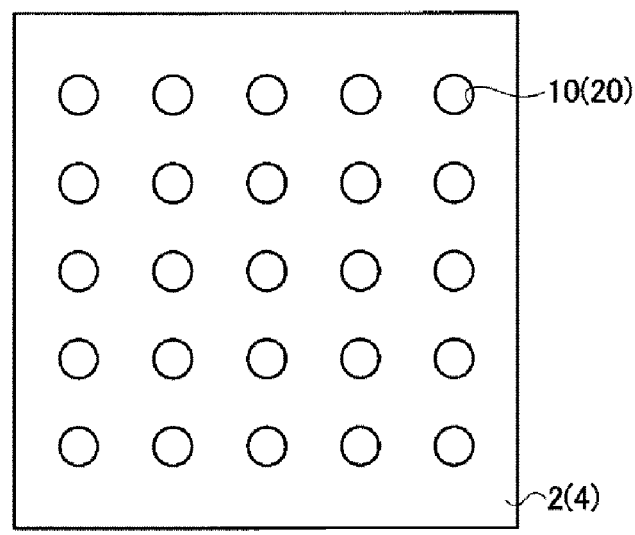
FIGS. 24A and 24B are views showing another mounting example of the $NO_x$ sensor according to the present embodiment.
Figure 24B:
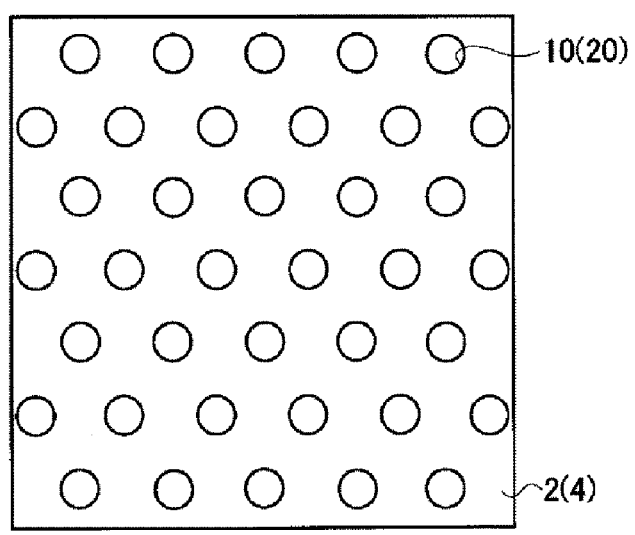

Among the examples of arrangement of the oxygen pumps 10 and the NO$_x$ sensors 20 mounted on the lower substrate 2 or the upper substrate 4 in the gas sensor apparatus to which the gas sensor according to the present embodiment is applicable, an example of a square lattice is schematically represented as shown in FIG. 24A, and an example of a triangular lattice is schematically represented as shown in FIG. 24B.

Figure 25A:
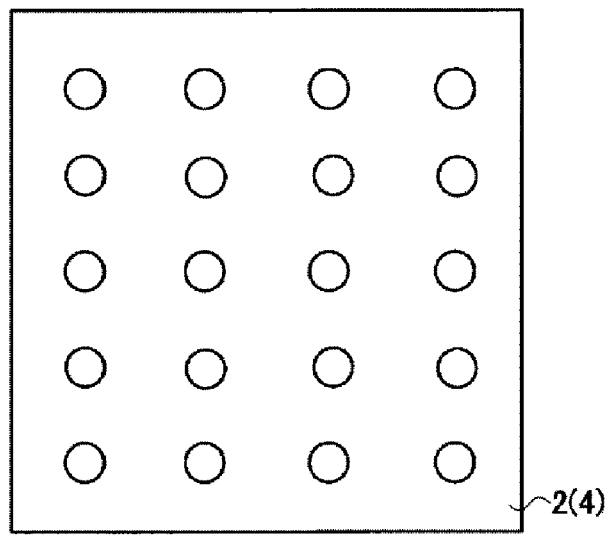
FIGS. 25A and 25B are views showing a further mounting example of the $NO_x$ sensor according to the present embodiment.
Figure 25B:
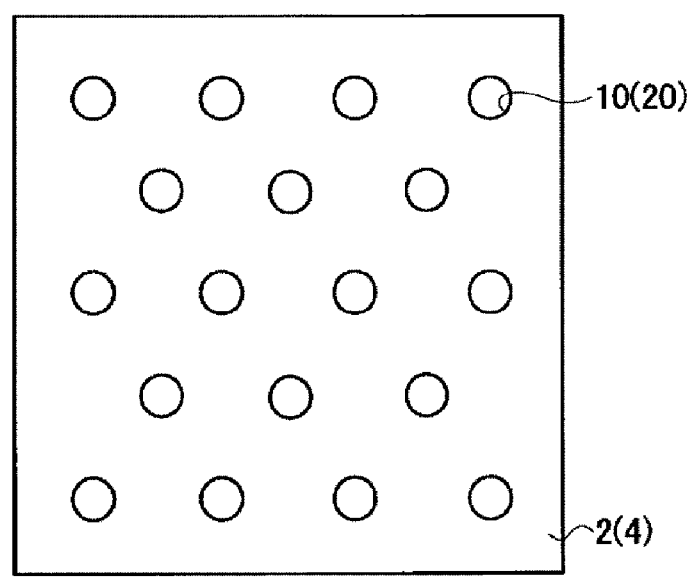

Among the examples of arrangement of the oxygen pumps 10 and the $NO_x$ sensors 20 mounted on the lower substrate 2 or the upper substrate 4 in the gas sensor apparatus to which the gas sensor according to the present embodiment is applicable, an example of a rectangular lattice is schematically represented as shown in FIG. 25A, and an example of a rhombic lattice (face-centered rectangular lattice) is schematically represented as shown in FIG. 25B.

As described above, in the gas sensor apparatus, the oxygen pumps 10 and the $NO_x$ sensors 20 may be two-dimensionally arranged on the lower substrate 2 or the upper substrate 4.

(Modifications of Electrode Arrangement)

Modifications of the electrode arrangement of the sensor portion SP of the gas sensor according to the present embodiment will be described.

Figure 26A:
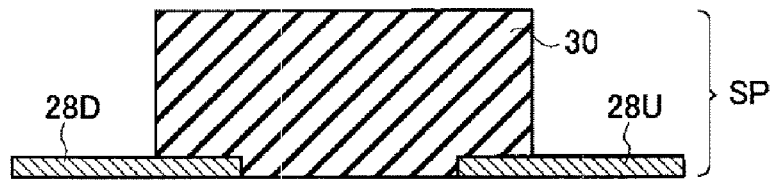
FIGS. 26A to 26H are views showing a modification of the electrode arrangement of the limit current type gas sensor shown in FIG. 13B.

As schematically shown in FIG. 26A, the electrodes 28D and 28U may be patterned on the same surface, and the electrodes 28U and 28D may be arranged so that the region between the electrodes 28U and 28D is covered with the solid electrolyte layer 30.

Figure 26B:
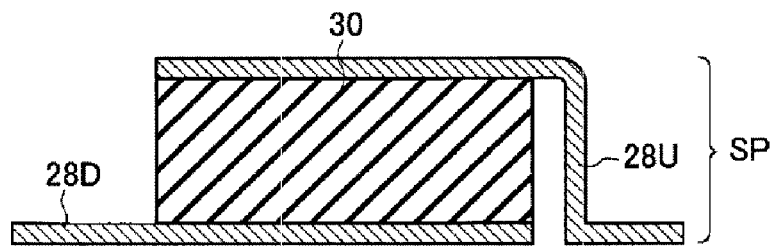

As schematically shown in FIG. 26B, the electrodes 28D and 28U may be arranged so as to completely cover the upper and lower surfaces of the solid electrolyte layer 30.

Figure 26C:
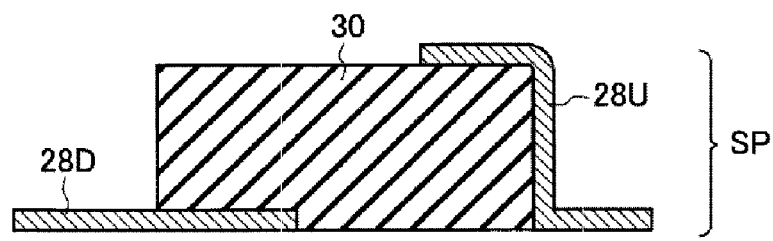

As schematically shown in FIG. 26C, one of the electrodes 28D and 28U may be arranged on a part of the lower surface of the solid electrolyte layer 30, and the other electrode 28D or 28U may be arranged on a part of the upper surface of the solid electrolyte layer 30.

Figure 26D:
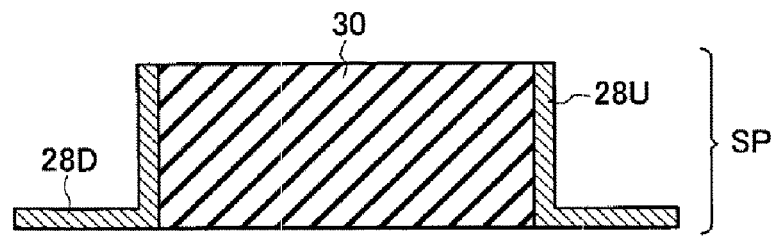

As schematically shown in FIG. 26D, the electrodes 28D and 28U may be arranged on the entire side surfaces of the solid electrolyte layer 30.

Figure 26E:
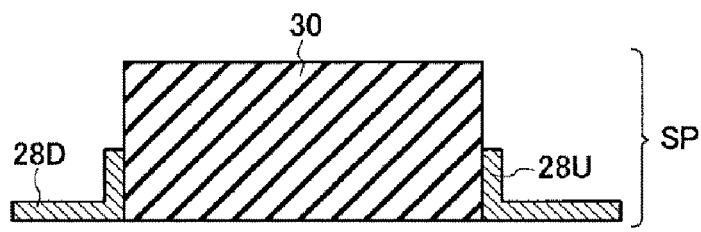

As schematically shown in FIG. 26E, the electrodes 28D and 28U may be arranged on a part of the side surfaces of the solid electrolyte layer 30.

Figure 26F:
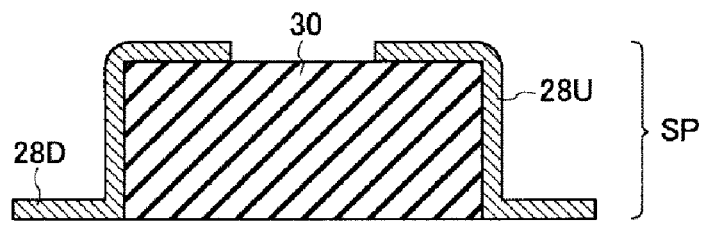

As schematically shown in FIG. 26F, the electrodes 28D and 28U may be arranged on the side surfaces and a part of the upper surface of the solid electrolyte layer 30.

Figure 26G:
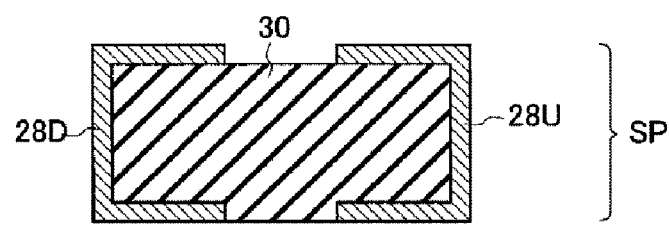

As schematically shown in FIG. 26G, the electrodes 28D and 28U may be arranged on the side surfaces of the solid electrolyte layer 30 so as to cover a part of each of the upper and lower surfaces.

Figure 26H:
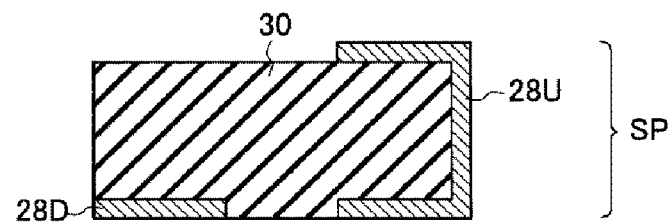

As schematically shown in FIG. 26H, one of the electrodes 28D and 28U may be arranged on one side surface of the solid electrolyte layer 30 and on a part of each of the upper and lower surfaces, and the other electrode 28D or 28U may be arranged on a part of the lower surface of the solid electrolyte layer 30.

(Modifications of Configuration of Sensor Portion)

Modifications of the configuration of the sensor portion SP of the gas sensor according to the present embodiment will be described.

Figure 27A:
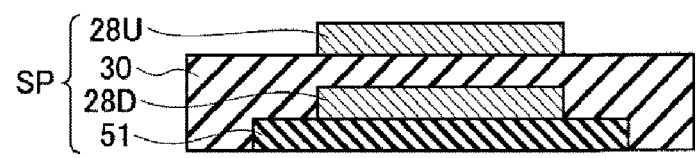
FIGS. 27A to 27F are views showing a modification of the sensor portion of the limit current type gas sensor shown in FIG. 13B.

As schematically shown in FIG. 27A, a porous film (porous oxide film) 51 having a gas diffusion structure in the in-plane direction may be further provided in the sensor portion SP.

Figure 27B:
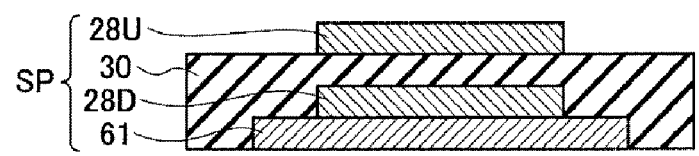

As schematically shown in FIG. 27B, a porous film (porous Pt film) 61 having a gas diffusion structure in the in-plane direction may be further provided in the sensor portion SP.

Figure 27C:
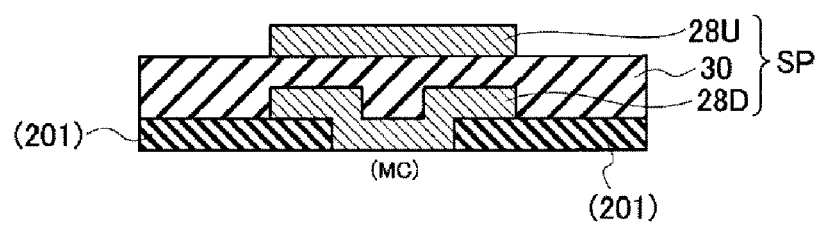

As schematically shown in FIG. 27C, a part of the lower electrode 28D of the sensor portion SP may protrude into the gas flow path MC.

Figure 27D:
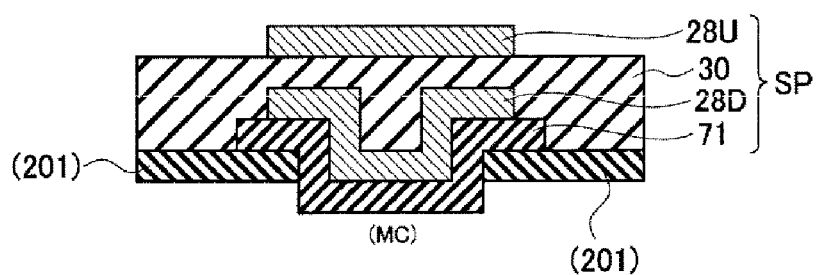

As schematically shown in FIG. 27D, a porous film (porous oxide film) having a gas diffusion structure in the in-plane direction) 71 may be provided between the lower electrode 28D of the sensor portion SP and the gas flow path MC.

Figure 27E:
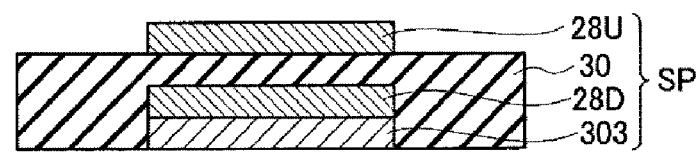

As schematically shown in FIG. 27E, a columnar film 303 having a gas throttling structure in the plane-perpendicular direction may be added to the sensor portion SP.

Figure 27F:
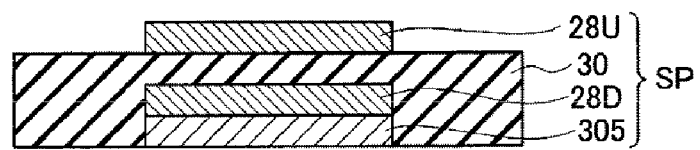

As schematically shown in FIG. 27F, a columnar electrode 305 having a gas throttling structure in the plane-perpendicular direction may be added to the sensor portion SP.

(Sensor Network)

Figure 28:
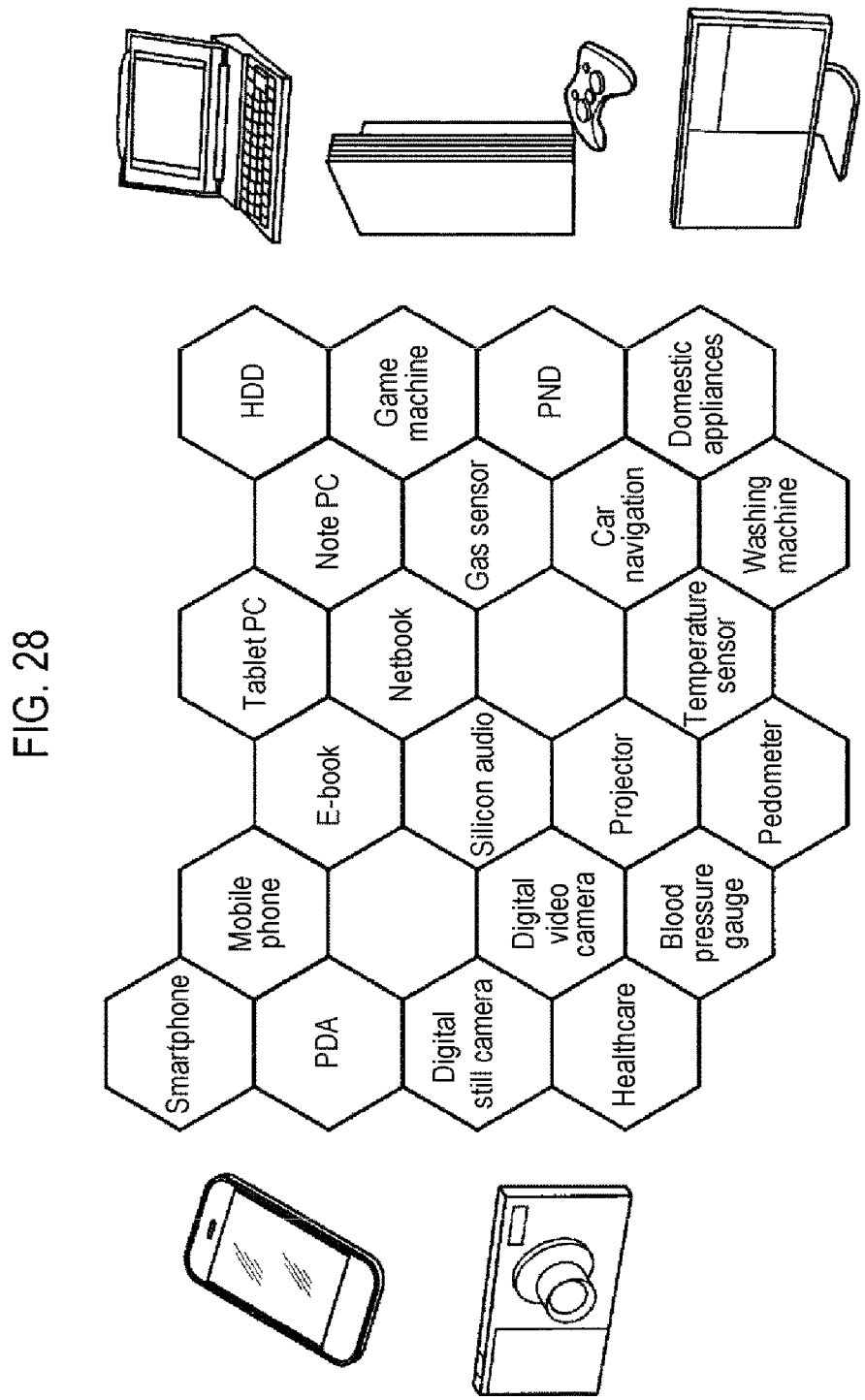
FIG. 28 is a schematic block configuration diagram of a sensor network to which the $NO_x$ sensor according to the present embodiment is applicable.

A schematic block configuration of a sensor network system to which the limit current type gas sensor according to each embodiment is applied is represented as shown in FIG. 28.

As shown in FIG. 28, the sensor network is a network in which a large number of sensors are connected to each other. A new approach using a sensor network has already begun in various fields such as factory, medicine/healthcare, transportation, construction, agriculture, environmental management, etc.

In these fields, it is desirable to use a sensor having a high response speed together with high durability. Therefore, it is desirable to use the limit current type gas sensor according to each embodiment, for example, as a humidity sensor. Since such a humidity sensor makes use of zirconia, it is excellent in durability. Therefore, it is possible to provide a highly reliable sensor network.

As described above, according to the present embodiment, it is possible to provide a nitrogen oxide based gas sensor which is easy to assemble, capable of improving the accuracy of sensing of a $NO_x$ gas and capable of increasing the sensitivity of detection of a $NO_x$ gas, an oxygen pump, a gas sensor apparatus, a manufacturing method of a gas sensor apparatus, and a sensor network system to which a gas sensor apparatus is applicable.

Other Embodiments

Although some embodiments have been described above, it is to be understood that the description and drawings constituting a part of the disclosure are illustrative and are not intended to limit the embodiments. Various alternative embodiments, examples and operational techniques will be apparent to those skilled in the art from this disclosure.

As described above, each embodiment includes various aspects not described here. For example, it is possible to detect the concentration of carbon dioxide by replacing zirconia with another material or by combining several materials.

A gas sensor apparatus to which the gas sensor according to the present embodiment is applicable may be applied to the exhaust gas of a motor vehicle or the like.

According to the present embodiment, it is possible to provide a nitrogen oxide based gas sensor which is easy to assemble, capable of improving the accuracy of sensing of a $NO_x$ gas and capable of increasing the sensitivity of detection of a $NO_x$ gas, an oxygen pump, a gas sensor apparatus, a manufacturing method of a gas sensor apparatus, and a sensor network system to which a gas sensor apparatus is applicable.

While certain embodiments have been described, these embodiments have been presented by way of example only, and are not intended to limit the scope of the disclosures. Indeed, the novel devices described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A gas sensor apparatus comprising:
    an enclosure including a lower substrate, an upper substrate disposed on the lower substrate, a first measurement space into which a measurement target gas is introduced via a first connection path, and a second measurement space connected to the first measurement space via a second connection path;
    a first oxygen pump disposed in the first measurement space and provided with a beam structure having a MEMS structure;
    a second oxygen pump disposed in the second measurement space and provided with a beam structure having a MEMS structure; and
    a nitrogen oxide based gas sensor disposed in the second measurement space and provided with a beam structure having a MEMS structure,
    wherein the first oxygen pump includes a plurality of first oxygen pumps provided in the first measurement space,
    wherein the first measurement space includes a plurality of space portions, and
    wherein the first oxygen pumps are respectively mounted in the space portions.

2. The gas sensor apparatus of claim 1, wherein each of the first oxygen pump and the second oxygen pump includes:
    a first substrate;
    a first heater disposed on the first substrate;
    a first lower electrode disposed on the first heater;
    a first solid electrolyte layer disposed on the first lower electrode;
    a first upper electrode disposed on a surface of the first solid electrolyte layer facing the first lower electrode and configured to introduce the measurement target gas;
    a first cavity portion formed in the first substrate; and
    a first gas flow path disposed so as to connect the first cavity portion and the first lower electrode,
    wherein each of the first oxygen pump and the second oxygen pump is configured to pump oxygen in the measurement target gas.

3. The gas sensor apparatus of claim 2, wherein the nitrogen oxide based gas sensor includes:
    a second substrate;
    a second heater disposed on the second substrate;
    a second lower electrode disposed on the second heater;
    a second solid electrolyte layer disposed on the second lower electrode;
    a second upper electrode disposed on a surface of the second solid electrolyte layer facing the second lower electrode and configured to introduce the measurement target gas;
    a second cavity portion formed in the second substrate; and
    a second gas flow path disposed so as to connect the second cavity portion and the second lower electrode,
    wherein the gas sensor is configured to detect a concentration of nitrogen oxide based on a concentration of oxygen in the measurement target gas.

4. The gas sensor apparatus of claim 3, wherein the first cavity portion and the second cavity portion have an open type structure.

5. The gas sensor apparatus of claim 3, wherein the second upper electrode is formed of a Pt film, the second solid electrolyte layer is formed of a YSZ film, and the second lower electrode is formed of a Pt/Ti film.

6. The gas sensor apparatus of claim 5, wherein a drive voltage at a predetermined temperature is set to 0.4 to 0.8 V in the second upper electrode and the second lower electrode.

7. The gas sensor apparatus of claim 3, wherein the nitrogen oxide based gas sensor further includes:
    a detection circuit configured to detect a concentration of nitrogen oxide in the measurement target gas in a limit current manner by applying a predetermined drive voltage between the second upper electrode and the second lower electrode.

8. The gas sensor apparatus of claim 7, wherein the detection circuit detects the concentration of the nitrogen oxide as a current value corresponding to a concentration of oxygen contained in the measurement target gas.

9. The gas sensor apparatus of claim 2, wherein the first upper electrode is formed of a Pt—Au film, the first solid electrolyte layer is formed of a YSZ film, and the first lower electrode is formed of a Pt/Ti film.

10. The gas sensor apparatus of claim 9, wherein a drive voltage at a predetermined temperature is set to 0.1 to 0.2 V in the first upper electrode and the first lower electrode.

11. The gas sensor apparatus of claim 1, wherein the second oxygen pump and the nitrogen oxide based gas sensor mounted in the second measurement space are disposed adjacent to each other in an in-plane direction.

12. The gas sensor apparatus of claim 1, wherein the first oxygen pump, the second oxygen pump, or the nitrogen oxide based gas sensor is mounted in the first measurement space and the second measurement space by a flip chip method.

13. A sensor network system comprising the gas sensor apparatus of claim 1.

14. The gas sensor apparatus of claim 1, wherein a first exhaust flow path is formed to connect to the first oxygen pump,
    wherein a second exhaust flow path is formed to connect to the second oxygen pump, and
    wherein a third exhaust flow path is formed to connect to the nitrogen oxide based gas sensor.

15. The gas sensor apparatus of claim 14, wherein a gas removed by the first oxygen pump is exhausted via the first exhaust flow path,
    wherein a gas removed by the second oxygen pump is exhausted via the second exhaust flow path, and
    wherein a gas detected by the nitrogen oxide based gas sensor is exhausted via the third exhaust flow path.

16. A gas sensor apparatus comprising:
    an enclosure including a lower substrate, an upper substrate disposed on the lower substrate, a first measurement space into which a measurement target gas is introduced via a first connection path, and a second measurement space connected to the first measurement space via a second connection path;
    a first oxygen pump disposed in the first measurement space and provided with a beam structure having a MEMS structure;

a second oxygen pump disposed in the second measurement space and provided with a beam structure having a MEMS structure; and a nitrogen oxide based gas sensor disposed in the second measurement space and provided with a beam structure having a MEMS structure, wherein the second oxygen pump and the nitrogen oxide based gas sensor mounted in the second measurement space are disposed to face each other in a plane-perpendicular direction.

17. A manufacturing method of a gas sensor apparatus, comprising:

mounting a first oxygen pump provided with a beam structure having a MEMS structure in a first measurement space which is provided in a lower substrate or an upper substrate constituting an enclosure and into which a measurement target gas is introduced via a first connection path, and mounting a second oxygen pump provided with a beam structure having a MEMS structure in a second measurement space connected to the first measurement space via a second connection path;

mounting a nitrogen oxide based gas sensor provided with a beam structure having a MEMS structure in the second measurement space; and bonding the lower substrate and the upper substrate.

* * * * *